Figure 1:
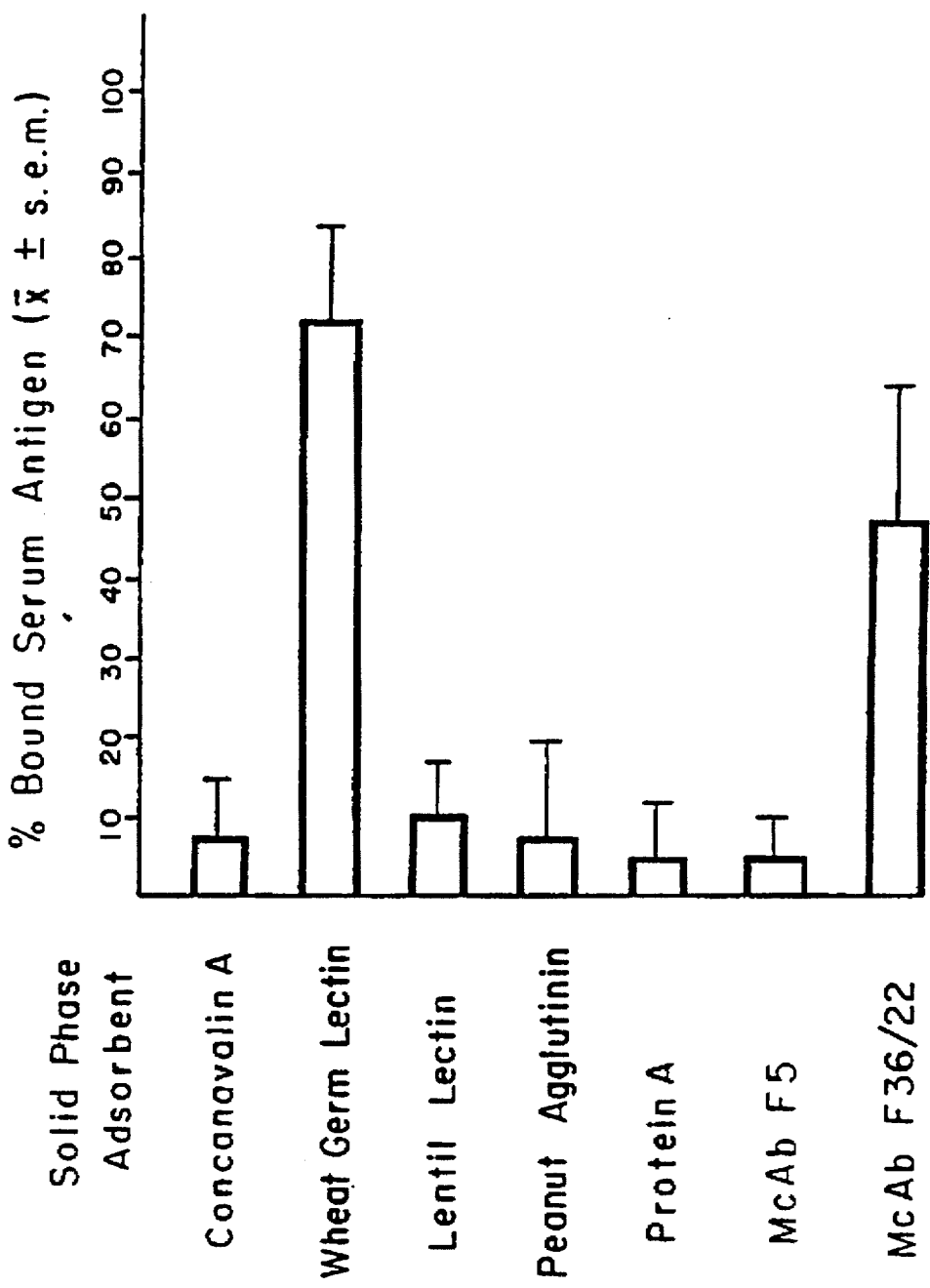

United States Patent [19]
Chu et al.

[11] Patent Number: 5,798,445
[45] Date of Patent: Aug. 25, 1998

[54] PURIFIED DUCTAL CARCINOMA ANTIGEN

[75] Inventors: Tsann Ming Chu, Williamsville; Lawrence D. Papsidero, Orchard Park, both of N.Y.

[73] Assignee: Health Research, Inc., Buffalo, N.Y.

[21] Appl. No.: 733,631

[22] Filed: Oct. 17, 1996

Related U.S. Application Data

[62] Division of Ser. No. 408,817, Sep. 18, 1989, Pat. No. 5,652,114, which is a division of Ser. No. 755,062, Sep. 11, 1985, Pat. No. 4,939,240, which is a continuation-in-part of Ser. No. 472,222, Mar. 4, 1983, abandoned.

[51] Int. Cl.$^6$ .......................... C07K 14/00; C07K 1/00; C07K 16/00; C12N 5/00
[52] U.S. Cl. .......................... 530/350; 530/350; 530/413; 530/388.2; 530/388.8; 530/388.85; 435/326; 435/330; 435/346
[58] Field of Search .......................... 424/130.1, 184.1; 530/350, 413, 388.85, 388.2, 388.8; 435/326, 330, 346

[56] References Cited

U.S. PATENT DOCUMENTS 4,486,530  12/1984  David et al. .......................... 435/7.91

FOREIGN PATENT DOCUMENTS

WO04313  12/1983  WIPO.

OTHER PUBLICATIONS

Abe et al., J. Immunology, 139:257–261, 1987.
Ceriani et al., Somatic Cell Genetics, 9:415–427 (1983).
Colcher et al., PNAS 78:3197–3203 (1981).
Croghan et al., Fed. Proc. 42(3) Abstract 1576.
Croghan, Dissertation Abstracts International 44(10) (1984).
Day, ISI Press, 124–127 (1983).
Johnson et al., Cancer Res. 46:850–857 (1986).
McGee et al., The Lancet, Jul. 3, 1982 pp. 7–10.
Penn State University 1992–94 Graduate Degree Programs Bulletin, pp. 52–57.
Sevier et al., Clin. Chem. 27:1797–1806 (1981).
Boon, Adv. Can Res, 58:177–210, 1992.
Ezzell, J. Nih Res, 1995, 7:46–49.
Spitler, Can Biotherapy, 1995, 10:1–3.
Papsidero et al., 1984, Cancer Research 44:4653–4657.
Papsidero et al., 1984, Molec. Immunol. 21:955–960.
Croghan et al., 1983, Cancer Research 43:4980–4988.
Croghan et al., 1984, Cancer Research 44:1954–1962.
Foster et al., 1982, Virchows Arch. [Pathpl. Anat.] 394:279–293.
Herlyn et al., 1980, Cancer Res. 40:717–721.
Masui et al., 1984, Cancer Res. 44:1002–1007.
Chu et al., 1973, J. Natl. Cancer Inst. 51:1119–1122.
Ceriani et al., 1977, Proc. Natl. Acad. Sci. USA 74:582–586.
Ceriani et al., 1982, Proc. Natl. Acad. Sci. USA 79:5420–54.
Bale et al., 1980, Cancer Research 40:2965–2972.
Gregoriadis, 1977, Nature 265:407–411.
Trouet et al., 1980 Recent Results Cancer Res. 75:229–235.
Gregoriadis, 1980, Pharmac. Ther. 10:103–118.
Raso et al., 1982, Cancer Research 42:457–464.
Krolick et al., 1982, Nature 295:604–605.
Krolick et al., 1980, Proc. Natl. Acad. Sci. USA 77:5419–542.
Ghose et al., 1978, J. Natl. Cancer Inst. 61:657–675.
Arnon et al., 1982, Immunological Rev. 62:5–27.
DeWeger et al., 1982, Immunological Rev., 62:29–45.
Seto et al., 1982, Cancer Research, 42:5209–5215.
Foster et al., 1982, Virchows Arch. [Pathol. Anat.] 394:295–305.
Scholm et al., 1982, Hybridomas in Cancer Diagnosis and Treatment edited by M.S. Mitchell and H.F. Oettgen, Raven Press, New York.
Nuti et al., 1982, Int. J. Cancer 29:539–454.
Colcher et al., 1983, Cancer Research 43:736–742.
Kufe et al., 1983, Cancer Research 43:851–857.
Hand et al., 1983, Cancer Research 43:728–735.
Taylor–Papadimitriou et al., 1981, Int. J. Cancer 28:17–21.
Arklie et al., 1981, Int. J. Cancer 28:23–29.
Papsidero et al., 1982, Hybridoma 1 (3):275–282.
Ciocca et al., 1982, Cancer Research 42:4256–4258.
Oldham, 1983, J. Clin. Oncol. 1:582–590.
Greene et al., 1980, Proc. Natl., Acad. Sci. USA 77:5115–5119.
Beverly, 1982, Nature 297:358–359.
Miller et al., 1982, The New England Journal of Medicine 306:517–522.
Young et al., 1981, Science 211:487–489.
Kirch et al., 1981, The J. of Immunol. 127:805–810.
Ritz et al., 1982, Blood 59:1–11.
Sears et al., Apr. 3, 1982, The Lancet, 762–765.
Herlyn et al., 1982, Proc. Natl. Acad. Sci. USA 79:4761–4765.
Adams et al, 1984, Proc. Natl. Acad. Sci. USA 81:3506–3510.

*Primary Examiner*—Lisa Feisee
*Assistant Examiner*—Susan Ungar
*Attorney, Agent, or Firm*—Pennie & Edmonds LLP

[57] ABSTRACT

Monoclonal antibodies to adenocarcinoma cells, and, in particular, breast carcinoma cells, are produced by a hybridoma formed by fusing mouse lymphocytes and mouse myeloma cells. The monoclonal antibodies are capable of shrinking solid tumors associated with human breast. The monoclonal antibodies identify an antigen associated with carcinomas of ductal lineage. The monoclonal antibodies, specifically, F36/22 monoclonal antibodies, can be used diagnostically and therapeutically.

3 Claims, 4 Drawing Sheets

PURIFIED DUCTAL CARCINOMA ANTIGEN

CROSS-REFERENCE TO RELATED APPLICATION

This application is a divisional of Ser. No. 07/408,817, filed Sep. 18, 1989, now U.S. Pat. No. 5,652,114, which is a divisional of Ser. No. 06/775,062, filed Sep. 11, 1985, currently U.S. Pat. No. 4,939,240 which in turn is a continuation-in-part of application Ser. No. 06/472,222, filed Mar. 4, 1983, presently abandoned, which is incorporated herein by reference.

TABLE OF CONTENTS
1. Introduction
2. Background of the Invention
   2.1. Monoclonal Antibodies
   2.2. Application of Monoclonal Antibodies to Cancer
   2.3 Monoclonal Antibodies to Mammary Cells
3. Summary of the Invention
4. Brief Description of the Figures
5. Description of the Invention
   5.1. The Antigen
   5.2. Somatic Cells
   5.3. Myeloma Cells
   5.4. Fusion
   5.5. Isolation of Clones and Antibody Detection
   5.6. Cell Propagation and Antibody Production
   5.7. In Vitro Diagnostic Uses for Monoclonal Antibodies to Human Breast Carcinoma
      5.7.1. Immunohistological and Immunocytological Applications
      5.7.2. Immunoserological Applications
   5.8. In Vivo Diagnostic and Therapeutic Uses for Monoclonal Antibodies to Human Breast Carcinoma
      5.8.1. Tumor Localization
      5.8.2. Passive Immunotherapy for Treatment of Human Cancer
      5.8.3. Treatment of Human Cancer with Monoclonal Antibody Conjugates
   5.9. Active Immunotherapy for Treatment of Human Cancer
6. Examples
   6.1. Breast Cell Lines and Tissues
   6.2. Immunization and Cell Fusion
   6.3. Isotyping of F36/22 Monoclonal Antibodies
   6.4. Immunoglobulin Preparations
   6.5. Cell-Surface Radioimmunoassay (CS-RIA)
   6.6. In Vitro Characterization of Monoclonal Antibody F36/22
      6.6.1. Detection and Binding of McAb F36/26 to Cultured Cells
      6.6.2. Quantitative Adsorption of McAb F36/22 to Cultured Cells
      6.6.3. Reciprocal Binding Inhibition
      6.6.4. In Vitro Cytotoxicity of McAb F36/22
      6.6.5. Reactivity of McAb F36/22 with Estrophilin Complexes
      6.6.6. Relationship Between Estradiol Concentration and McAb F36/22 Binding Levels
   6.7. Characterization of the Antigen Recognized by Monoclonal Antibody F36/22
      6.7.1. Solid-Phase Adsorption of BT-20 Breast Carcinoma Antigen by Lectins
      6.7.2. Antigen Modulation
      6.7.3. Release of Antigen Recognized by McAb F36/22 by Tumor Cells
      6.7.4. Gel Filtration Chromatography of MCF-7 Antigen Recognized by McAb F36/22
      6.7.5. Effect of Enzyme Digestions on Cell Surface Antigenicity
   6.8. Detection of Ductal Carcinoma Antigen in Breast Cancer Sera Using Monoclonal Antibody F36/22
      6.8.1. Enzyme Immunoassay Procedure
      6.8.2. Biochemical Characteristics of Circulating Sera
      6.8.3. Solid Phase Adsorption of Serum Antigen
   6.9. Immunoaffinity Isolation of Ductal Carcinoma Antigen Using Monoclonal Antibody F36/22
      6.9.1. Purification of Antigen
      6.9.2. Size Fractionation of Antigen
      6.9.3. Polyacrylamide Gel Electrophoresis
      6.9.4. Enzyme Immunoassay
      6.9.5. Physical Characteristics of Purified Antigen
      6.9.6. Lectin Binding Ability of Purified Antigen
      6.9.7. Effects of Physical Treatment, Chemical Modifications and Enzymes on the Binding of McAb F36/22 to Purified Antigen
   6.10. In Vitro Immunohistological Applications of Monoclonal Antibody F36/22
      6.10.1. Immunoperoxidase Staining of Tumor Specimens by McAb F36/22
      6.10.2. Immunoreactivity of McAB F36/22 With Normal Mammary Tissue, Membrane Preparations and Milk
      6.10.3 Immunoperoxidase Staining of Human Breast Tissues and Tumors
      6.10.4. Effect of Varying McAb F36/22 Concentration and Incubation Times on Immunoperoxidase Staining Results
      6.10.5. Estrogen Receptor Levels and Immunoperoxidase Staining
   6.11. In Vivo Applications of Monoclonal Antibody F36/22
      6.11.1. Experimental Induction of Solid Tumors in Mice
      6.11.2. McAb F36/22 Targeting: In Vivo Tumor Localization
      6.11.3. In Vivo Passive Immunotherapy with McAb F36/22

1. INTRODUCTION

This invention relates to the production of and applications for monoclonal antibodies specific for tumor antigens. More particularly, this invention relates to monoclonal antibodies against cell surface antigenic determinants expressed maximally on breast carcinomas and also present on other adenocarcinomas. Monoclonal antibodies capable of reacting with cell-surface antigens are of value for the immunoclassification and detection of disease and represent novel agents for immunotherapy. The monoclonal antibodies of this invention possess distinctive characteristics and capabilities which make them suitable for in vitro clinical diagnostic purposes. Moreover, they are of great potential importance for in vivo tumor localization and cancer therapy in humans.

The monoclonal antibodies exhibit a high level of binding to breast carcinoma cells and are capable of experimental in vivo tumor localization. They bind to well-differentiated as well as to poorly-differentiated tumors. The antigen recognized is a cell surface component associated with carcinomas of ductal lineage that remains unmodulated after exposure to antibody. The monoclonal antibodies exhibit the ability to fix human complement. Most importantly, the monoclonal antibodies of this invention are capable of inducing a rapid and significant volume reduction of established, progressively growing, solid human breast tumors xenografted in animals (mice). The tumoricidal effectiveness is quite remarkable with tumor volume shrinkage of greater than 70% in short intervals (three days) after administration of low doses (100 µg) of antibody. Immunotherapy occurs passively, independently of any cytotoxic compounds.

The invention provides methods for production of the monoclonal antibodies by hybridoma techniques. Once cloned, cell lines can be maintained continuously to produce an unlimited homogeneous monoclonal antibody population that can be isolated and/or purified and used clinically for in vitro immunohistological, immunocytological or immunoserological diagnosis, in vivo diagnosis by localization of tumors and metastases, and immunotherapy of human cancers, particularly those of the breast.

2. BACKGROUND OF THE INVENTION

2.1. MONOCLONAL ANTIBODIES

Kohler and Milstein are generally credited with having devised the techniques that successfully resulted in the formation of the first monoclonal antibody-producing hybridomas [G. Kohler and C. Milstein, Nature 256:495–497 (1975); Eur. J. Immunol. 6:511–519 (1976)]. By fusing antibody-forming cells (spleen lymphocytes) with myeloma cells (malignant cells of bone marrow primary tumors) they created a hybrid cell line, arising from a single fused cell hybrid (called a hybridoma or clone) which had inherited certain characteristics of both the lymphocytes and myeloma cell lines. Like the lymphocytes (taken from animals primed with sheep red blood cells as antigen), the hybridomas secreted a single type of immunoglobulin specific to the antigen; moreover, like the myeloma cells, the hybrid cells had the potential for indefinite cell division. The combination of these two features offered distinct advantages over conventional antisera. Whereas antisera derived from vaccinated animals are variable mixtures of polyclonal antibodies which never can be reproduced identically, monoclonal antibodies are highly specific immunoglobulins of a single type. The single type of immunoglobulin secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences [generally 6–7 amino acids in length (M. Z. Atassi, Molec. Cell. Biochem. 32:21–43 (1980)] within the entire protein molecule. Hence, monoclonal antibodies raised against a single antigen may be distinct from each other depending on the determinant that induced their formation; but for any given clone, all of the antibodies it produces are identical. Furthermore, the hybridoma cell line can be reproduced indefinitely, is easily propagated in vitro or in vivo, and yields monoclonal antibodies in extremely high concentration.

2.2. APPLICATION OF MONOCLONAL ANTIBODIES TO CANCER

Monoclonal antibodies presently are being applied by investigators to the diagnosis and treatment of cancer [For a general discussion of the topic, see Hybridomas in Cancer Diagnosis and Treatment, Mitchell, M. S. and Oettgen, H. F., (eds.), Progress in Cancer Research and Therapy, Vol. 21, Raven Press, New York (1982)]. It has been reported that monoclonal antibodies have been raised against tumor cells [U.S. Pat. No. 4,196,265], carcinoembryonic antigen [U.S. Pat. No. 4,349,528], and thymocytes, prothymocytes, monocytes and suppressor T cells [U.S. Pat. Nos. 4,364,933; 4,364,935; 4,364,934; 4,364,936; 4,364,937; and 4,364,932]. Recent reports have demonstrated the production of monoclonal antibodies with various degrees of specificity to several human malignancies, including mammary tumor cells [Colcher, D. et al., Proc. Natl. Acad. Sci. U.S.A. 78:3199–3203 (1981)], lung cancers [Cuttitta, F. et al., Proc. Natl. Acad. Sci: U.S.A. 78:495–4595 (1981)] malignant melanoma [Dippold, W. G. et al., Proc. Natl. Acad. Sci. U.S.A., 77:6114–6118 (1980)], colorectal carcinoma [Herlyn, M. et al., Proc. Natl. Acad. Sci. U.S.A. 76:1438–1442 (1979)], lymphoma [Nadler, L. M. et al., J. Immunol. 125:570–577 (1980)], and neuroectodermal tumors [Wikstrand, C. J. and Bigner, D. C., Cancer Res., 42:267–275 (1982)].

Investigators have noted the potential immunotherapeutic value of monoclonal antibodies and some investigators have investigated therapeutic efficacy in both animal and human subjects [Miller, R. A. et al., New Eng. J. Med. 306:517–522 (1982); Ritz, J. and Schlossman, S., Blood, 59:1–11 (1982); and Kirch, M. E. and Ulrich, H. J. Immunol., 127:805–810 (1981)]. Although most studies have described the effects of cytotoxic drug-antibody conjugates, [Beverly, P. C. L., Nature, 297:358–9 (1982); Krolick, K. A. et al., Nature, 295:604–5 (1982); Krolick, K. A. et al., Proc. Natl. Acad. Sci. U.S.A., 77:5419–23 (1980); Arnon, R. and Sela, M., Immunol. Rev., 62:5–27 (1982); Raso, V. et al., Cancer Res., 42:457–64 (1982); and DeWeger, R. A. and Dullens, H. F. J., Immunol. Rev. 62:29–45 (1982)], experimental and clinical studies on passive immunotherapies have been attempted [Sears, H. F. et al., Lancet, i:762–65 (1982); Rosenberg, S. A. and Terry, W. D., Cancer Res., 25:323–88 (1977); Herlyn, D. M. et al., Cancer Res., 40:717–21 (1980); Scheinberg, D. A. and Strand, M., Cancer Res. 42:44–9 (1982); Koprowski, H. et al., Proc. Natl. Acad. Sci. U.S.A., 75:3405–9 (1978); and Young, Jr., W. W. and Hakomori, S.-L, Science, 211:487–9 (1981)]. In the experimental setting, however, most studies have dealt with the concurrent administration of monoclonal antibody and tumor inoculum, or administration within several days of the implantation of tumor cells, resulting in a decreased tumor take or growth rate of xenografts. In this context, these data form a basis for the immunoprophylaxis of tumor development. It is an object of the present invention to provide monoclonal antibodies demonstrating a therapeutic effect on progressively-growing established tumors. To our knowledge, prior to this invention, tumor volume reduction against well established progressively growing solid tumors with the use of passive monoclonal antibody has not been reported.

2.3 MONOCLONAL ANTIBODIES TO MAMMARY CELLS

Several investigators have reported on the production of monoclonal antibodies against epitopes of various normal and malignant mammary cell components. [Arklie, J. et al., Int. J. Cancer, 28:23–29(1981); Ciocca, D. R. et al., Cancer Res., 42:4256–4258(1982); Colcher, D. et al., Proc. Natl. Acad. Sci., U.S.A. 78:3199–3203 (1981); Foster, C. S. et al., Virchows Arch. Pathol. Anat., 394:279–293(1982); Greene, G. L. et al., Proc. Natl. Acad. Sci. U.S.A., 77:5115–5119 (1980)]; McGee, JO'D. et al., Lancet 2:7–11(1982); Nuti, M.

et al., Int. J. Cancer, 291:539–545(1982); and Taylor-Papadimitriou, J. et al., Int. J. Cancer, 28:17–21(1981)]. Many of the antigens recognized above are differentiation-related; therefore these antibodies are most suited to histologically assess the differentiated status or grade of tumor specimens. For example, monoclonal antibodies directed against several antigens of human milk-fat-globule membranes have been produced. These antibodies have proven useful in studying the derivation of cell cultures, in evaluating the phenotypic expression of antigens in neoplastic transformation, and have served as differentiation markers in breast cancer, and as immunodiagnostic reagents in the quantitation of antigens in the sera of breast cancer patients [Arklie, J. et al., Int. J. Cancer, 28:23–29(1981); Ceriani, R. L. et al., Proc. Natl. Acad. Sci. U.S.A., 74:582–586(1977); Ceriani, R. L. et al., Proc. Natl. Acad. Sci., 79:5420–5424 (1982); Foster, C. S. et al., Virchows Arch. Pathol. Anat., 394:279–293(1982); and Taylor-Papadimitriou, J. et al., Int J. Cancer, 28:17–21(1981)]. However, there is further need for monoclonal antibodies which are differentiation-unrelated and of use to detect antigen occurring in poorly-differentiated breast tumors. It is an object of this invention to provide such monoclonal antibodies. Such reagents may reflect subtle biochemical or antigenic differences in breast cancer, independent of tumor grade. The use of such antibodies can add significant information regarding functional classifications of individual breast tumors to augment clinical classifications.

The pattern of staining for the monoclonal antibody of this invention is distinct from the reactivities of previously described monoclonal antibodies which recognize antigens expressed by breast tumors. Arklie et al. [supra] have described monoclonal antibodies directed against human milk-fat-globule membranes. These antibodies showed a stronger staining reaction with well-differentiated (grade I) ductal carcinomas than undifferentiated (grade III) tumors. By comparison, the monoclonal antibody provided herein stained poorly-differentiated tumors equally well as well-differentiated breast carcinoma specimens. Therefore, the monoclonal antibody identifies a sub-class of breast carcinomas which is histologically indistinguishable from tumors lacking antigen expression. Nuti et al. [supra] have produced monoclonal antibodies against human metastatic breast carcinoma cells which have been used to indicate tumor antigen heterogeneity, but which failed to react with normal and benign mammary tissues or uterus. Other reported monoclonal antibodies directed against carcinoma-associated antigens [McGee et al., supra] also did not react with any benign conditions of the breast and very few normal tissues. Foster et al. [supra] have also reported the production of monoclonal antibodies which were used to show significant heterogeneity of antigen expression within breast tumors, but whose specifities are distinct from the monoclonal antibodies of the present invention.

3. SUMMARY OF THE INVENTION

Prior to the present invention, applicants believe there has been no report of a clinically useful preparation of monoclonal antibodies which, upon passive administration, is capable of reducing the volume of well established, progressively growing solid tumors associated with the human breast. In fact, it is applicants' belief that volume reduction of any other established and growing solid tumors with the use of passive monoclonal antibody immunotherapy has not been reported. The present invention provides methods and compositions for producing novel monoclonal anti-breast carcinoma antibodies with specific binding, cytotoxic and tumor shrinkage capabilities and encompasses the use of said antibodies for cancer immunodiagnosis and passive immunotherapy in humans.

Specifically, the invention provides novel hybridoma-derived monoclonal antibodies which react with a determinant (epitope) located both on differentiated mammary duct epithelia and on certain breast carcinomas; the monoclonal antibodies do not react with estrophilin, bone marrow stem cells or lymphoid cells. In contrast to the expression of previously described differentiation antigens, the epitope recognized by the monoclonal antibodies of this invention is also found in a high percentage of poorly-differentiated carcinomas of the human breast. The extent of antigenic expression, as detected by the monoclonal antibodies, is similar for well and poorly differentiated tumors and is independent of the histological characteristics of the tumor. The monoclonal antibodies can be used immunologically to sub-classify tumors which are histologically indistinguishable by conventional histopathological staining techniques and to establish phenotyping of breast cancer. Hence, the monoclonal antibodies of the present invention represent new in vitro immunodiagnostic reagents for the early and accurate detection of certain cancers.

The epitope recognized by the monoclonal antibody of this invention is also present on other adenocarcinomas, including those of the colon, ovary, uterus, pancreas and prostate (see Section 6.10.1), although the antigenic determinant is expressed at a lower level than in breast cancer. The normal tissue of these histotypes (colon, ovary, uterus, pancreas, prostate, etc.) contain no detectable levels of the determinant. Therefore, the expression of the antigen recognized by the monoclonal antibodies may be associated with the neoplastic development of these histotypes. Hence, the monoclonal antibodies of the present invention represent a new diagnostic indicator of certain cancers in these tissues. Because certain adenocarcinomas do not contain detectable levels of the epitope, the monoclonal antibodies identify antigenic differences which can be prognostically significant.

In addition to their use as in vitro immunohistological reagents for cancer diagnosis, the monoclonal antibodies of the present invention can be used diagnostically in vivo. Because of their ability to target breast carcinoma cells in vivo, the monoclonal antibodies can be used in tumor localization and in the monitoring of metastases.

Furthermore, the monoclonal antibodies provided herein can be used as in vitro immunoserological and immunocytological reagents on body fluids to detect the presence of the specific antigen and/or cells bearing antigen. The monoclonal antibodies thereby permit non-invasive diagnosis of certain breast carcinomas and other cancers.

The present invention also contemplates the use of the monoclonal antibodies for serodetection of ductal carcinoma antigen to be used in the differential diagnosis of certain carcinomas of ductal lineage.

Most importantly, the hybridoma-derived monoclonal antibodies of the present invention represent new immunotherapeutic agents for the treatment of human breast cancer. The monoclonal antibodies are capable of inducing a rapid and significant reduction of progressively growing adenocarcinomas associated with the human breast. The tumoricidal effectiveness at low doses of the monoclonal antibodies, the high incidence of antigen expression in biopsies of breast cancer patients and the high specific binding of the monoclonal antibodies to certain breast tumors, the absence of modulation of the antigen recognized and the ability of the monoclonal antibodies to fix human complement and eradicate cancer cells independent of other cytotoxic agents are indications of the usefulness of the monoclonal antibodies in human breast cancer therapy.

The present invention provides methodologies useful in research for the evaluation of parameters associated with the use of monoclonal antibodies against human tumors in passive human immunotherapy. The monoclonal antibodies can be used as probes to investigate the roles of antigen density, tumor growth rates, tumor size, cellular heterogeneity and other variables in the susceptibility of tumors to immunotherapy.

The invention contemplates the use of the monoclonal antibodies provided herein in covalent combination with cytotoxic or chemotherapeutic molecules. For instance, the monoclonal antibodies can be conjugated to certain cytotoxic compounds, including, but not limited to, radioactive compounds, diphtheria toxin (chain A), ricin toxin (chain A) adriamycin, chlorambucil or daunorubicin, to enhance their tumoricidal effectiveness. The invention also contemplates the covalent combination of the monoclonal antibodies with carbohydrate-active reagents such as, but not limited to, glycosidases, to unmask the cell surface antigen recognized, thereby increasing antibody binding and tumoricidal effectiveness.

The present invention further contemplates the use of the monoclonal antibodies in immunoadsorption procedures to effectively separate breast cancer cells from marrow elements based upon antibody binding, and in complement-mediated cytolytic procedures to eliminate malignant cells while sparing bone marrow stem cells. Because such procedures require a tumor antigen, such as the one recognized by the monoclonal antibodies of this invention, which is not found on bone marrow stem cells or lymphoid cells, the monoclonal antibodies represent a reagent useful for eliminating disseminated breast cancer cells from autologous bone marrow.

Because the monoclonal antibodies are produced by hybridoma techniques, the present invention provides theoretically immortal cell lines capable of consistently producing high titers of single specific antibodies against a distinct breast carcinoma antigen. This is a distinct advantage over the traditional technique of raising antibodies in immunized animals where the resulting sera contain multiple antibodies of different specificities that vary in both type and titer with each animal, and, in individual animals, with each immunization.

The invention further provides purified ductal carcinoma antigen, all or part of which antigen may serve as the basis for a vaccine against cancers characterized by the presence of tumor cells expressing the antigen. The invention also contemplates active immununotherapies involving the administration to humans of such a vaccine. The invention further contemplates preparing anti-idiotype antibodies to the monoclonal antibodies of this invention and preparing anti-idiotype vaccines to be administered to humans for treatment of cancer.

The invention further provides purified ductal carcinoma antigen, all or part of which antigen may serve as the basis for a vaccine against cancers characterized by the presence of tumor cells expressing the antigen. The invention also contemplates active immunotherapies involving the administration to humans of such a vaccine. The invention further contemplates preparing anti-idiotype antibodies to the monoclonal antibodies of this invention and preparing anti-idiotype vaccines to be administered to humans for treatment of cancer.

4. BRIEF DESCRIPTION OF THE FIGURES

FIG. 1. graphically illustrates solid-phase adsorption of serum antigen. Specimens of breast cancer sera (N=6) were allowed to react with various solid-phase adsorbents. Non-derivatized Sepharose served as a negative control (i.e., 0% bound antigen). After incubation, each supernatant was assayed for antigen activity (triplicate measurements), and this value was used to calculate the percentage of bound antigen. McAb F36/22:Sepharose was used as a positive control for these experiments. Binding specificities: concanavalin A, α-D-mannosyl groups; wheat germ lectin, β-N-acetylglucosaminyl groups; peanut agglutinin, β-N-acetylglucosaminyl groups; Protein A, Fc$_\gamma$-immunoglobulin domain. McAb F5 reacts with an antigen specific for prostate tissue. Statistical evaluations (Student's t test) indicated that the solid-phase adsorbents prepared from wheat germ lectin and McAb F36/22 bound statistically significant (p less than 0.01) amounts of serum antigen as compared to control Sepharose.

Figure 2:
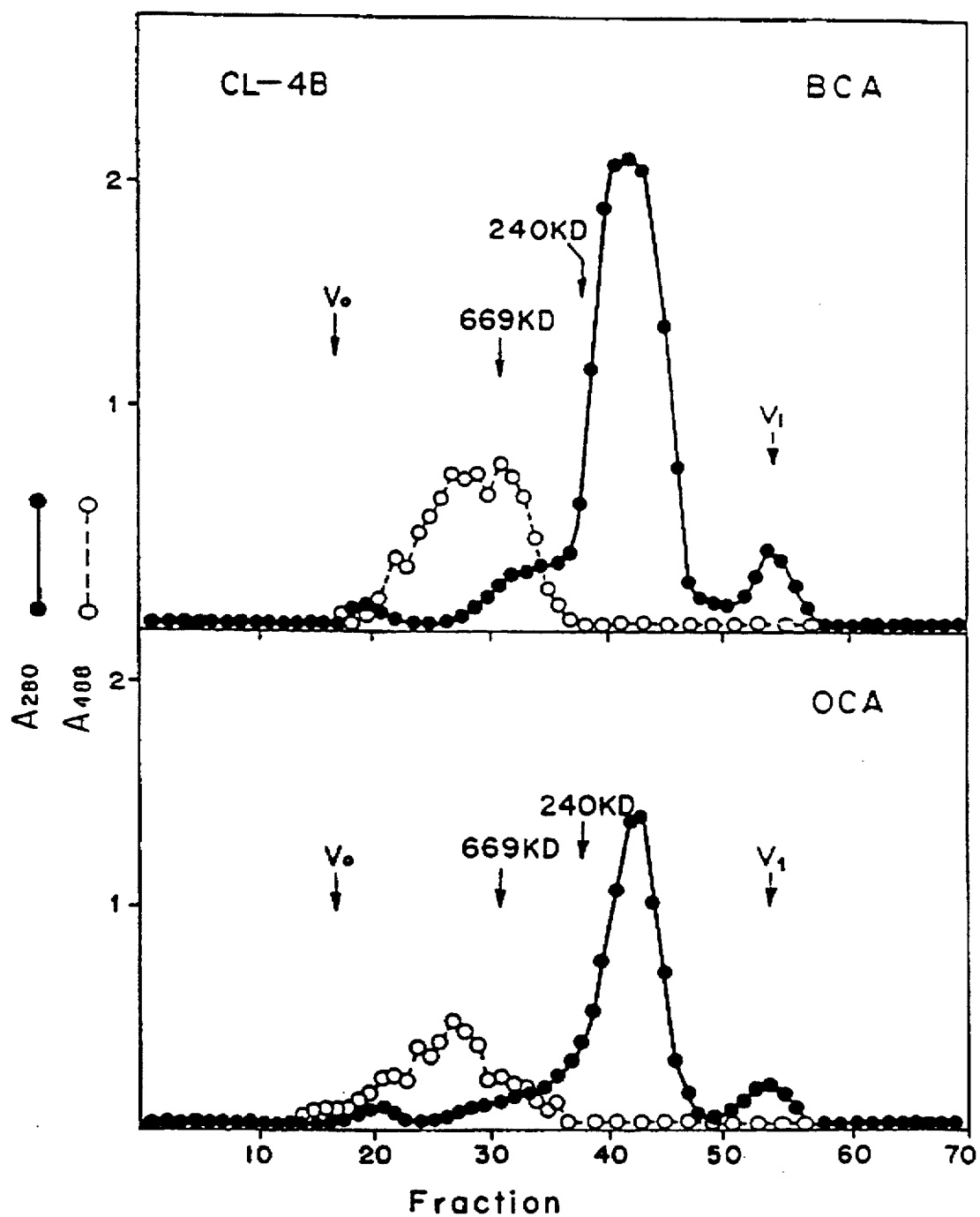

FIG. 2. graphically illustrates molecular sieve chromatography of malignant effusions obtained from patients with breast cancer (BCA) or ovarian cancer (OCA). Fractions were evaluated for protein (absorbance at 280 nm) and antigen content (absorbance at 480 nm). In all fluids studied peak antigen activity eluted in the included volume, ahead of the 669,000 molecular weight marker protein. The column was precalibrated using blue dextran [void volume ($V_o$)], bovine thyroglobulin (669 KD), bovine catalase (240 KD) and phenol red [total bed volume ($V_t$)].

Figure 3:
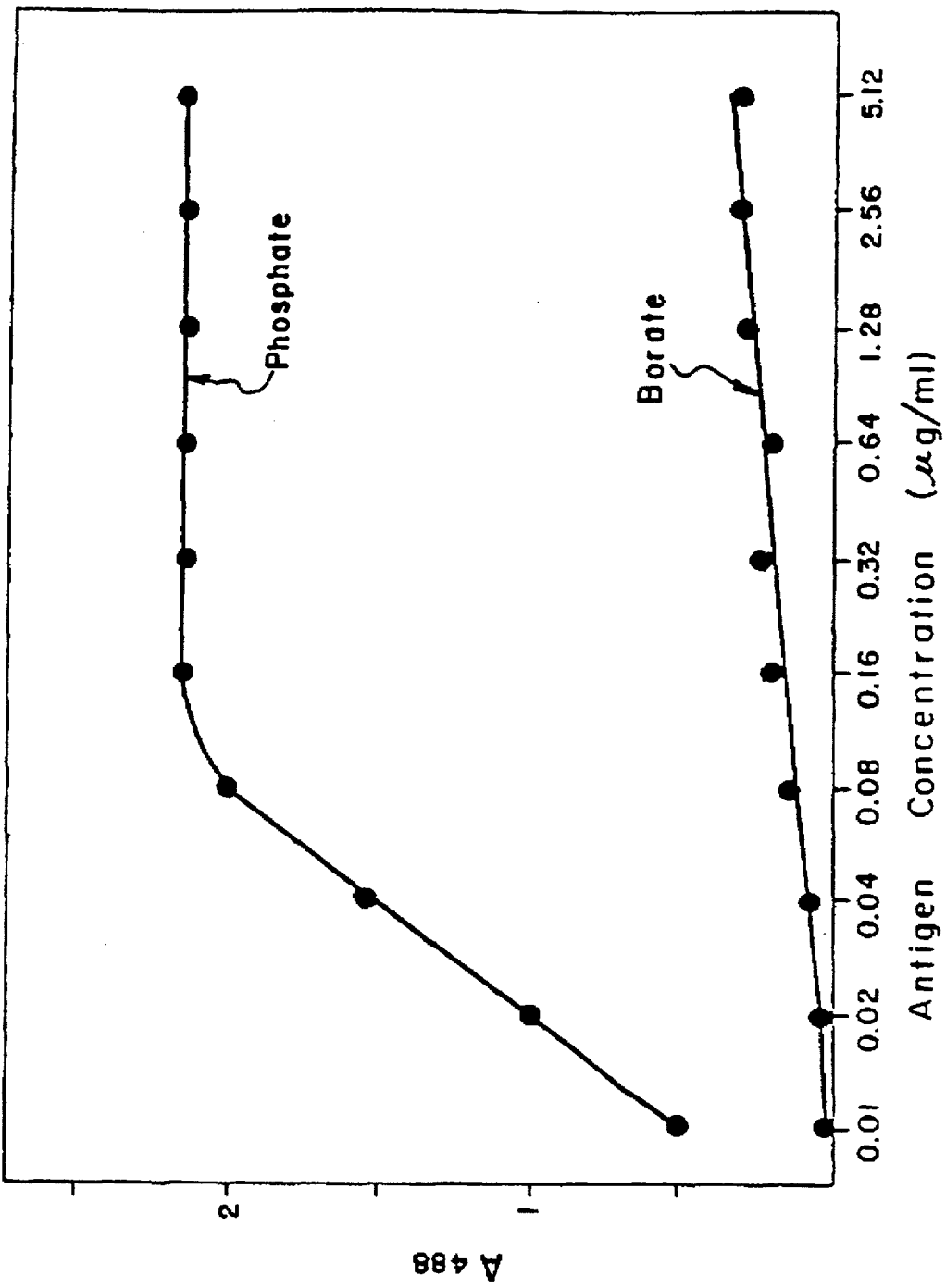

FIG. 3. graphically illustrates an enzyme immunoassay of the immunoaffinity-purified ductal carcinoma antigen from malignant effusion. The assay was performed in the presence of standard assay buffer containing pH 7.0 phosphate salts or borate salts at pH 7.0.

Figure 4:
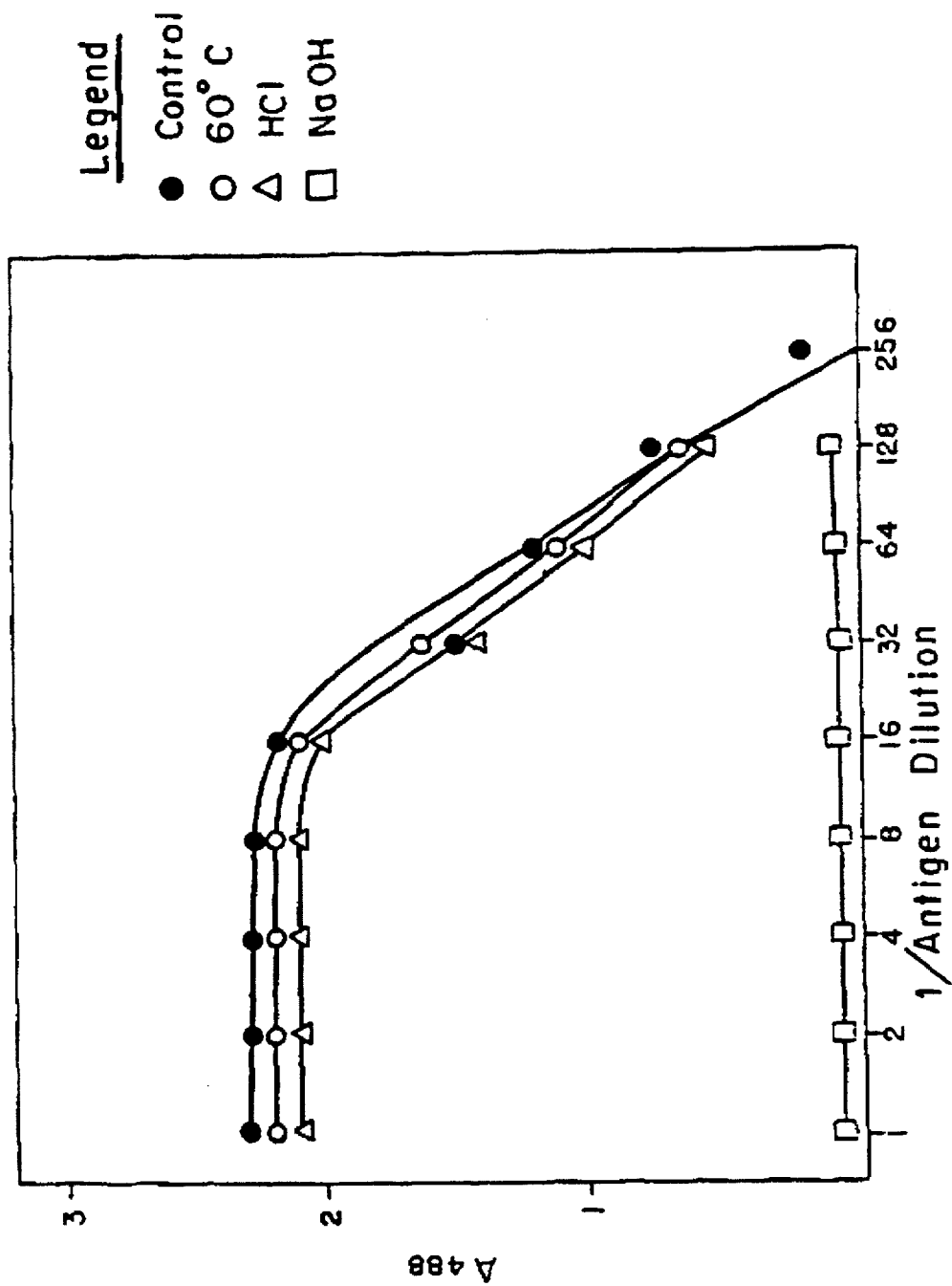

FIG. 4. graphically illustrates the stability of immunopurified antigen after acid, base and heat treatment. Antigen was incubated for 5 hours at 60° C. in the presence or absence of 0.1N NaOH or 0.1N HCl. Residual activity was determined using an enzyme immunoassay procedure (absorbance at 488 nm).

5. DESCRIPTION OF THE INVENTION

5.1. THE ANTIGEN

In the embodiment of the invention described in Section 6.2., MCF-7 breast carcinoma cells were used as 'antigen'. However, as demonstrated by experiments described in Section 6.6.1., 6.10.1., and 6.10.3., the epitope recognized by the antibody of this invention is present on the surface of several cultured cell lines as well as cells present in certain extra-mammary tumors. Hence, these cells also represent potential 'antigen' or sources of antigen with which to immunize animals to obtain somatic cells for fusion.

For example, the BT-20, MDA-MB-157, and to a lesser extent, SK-BR-3 breast carcinoma cell lines can be used as immunogens. Non-breast carcinoma cell lines, including PANC-1 (pancreas carcinoma) and HT-29 (colon carcinoma) also represent potential candidates as immunogen in other embodiments of the invention. Furthermore, cells derived from intensely-staining benign or malignant breast tissues listed in TABLE XI. can be used. Similarly, cells derived from positively-staining extra-mammary tumors listed in TABLE XI, for instance ovarian, colon, endometrial, renal, bronchogenic, etc., carcinomas or ovarian cystadenomas, can be used as immunogen.

Cells or fluids derived from pleural effusions of breast cancer patients (see Section 6.7.3.) and antigen isolated from cell lysates as described in Section 6.7.4. are also potential candidates with which to immunize animals and humans.

In the embodiment of the invention described herein, monoclonal antibodies raised against a breast tumor line identified an antigen associated with carcinomas of ductal lineage and occurring on a limited number of normal ductal elements. The antigen, hereinafter referred to as ductal carcinoma antigen (DCA), has been detected in human body fluids such as malignant effusions, lymph, sera and thoracentesis. Electrophoretic analysis of the antigen demonstrated the isolation of a single high molecular weight glycoprotein exhibiting an isoionic point near pH 4.2 and a density of approximately 1.45/ml. Although highly reactive with wheat germ lectin, a negligible or weak interaction was observed with concanvalin A, lentil lectin and peanut agglutinin. The antigen was immune-precipitable, indicating the occurrence of multiple monoclonal antibody-binding sites, and was resistant to heat and acid treatments. Antigenicity was not perturbed following protease or neuraminidase treatments, but was affected upon exposure to alkaline conditions. These data suggest that monoclonal antibody F36/22 recognizes a high molecular weight component occurring in circulation as a mucin-like glycoprotein (see Section 6.8).

5.2. SOMATIC CELLS

Somatic cells with the potential for producing antibody and, in particular B lymphocytes, are suitable for fusion with a B-cell myeloma line. Those antibody-producing cells that are in the dividing plasmablast stage fuse preferentially. Somatic cells may be derived from the lymph nodes, spleens and peripheral blood of primed animals and the lymphatic cells of choice depends to a large extent on their empirical usefulness in the particular fusion system. Once-primed or hyperimmunized animals can be used as a source of antibody-producing lymphocytes. Mouse lymphocytes give a higher percentage of stable fusions with the mouse myeloma lines described in Section 5.3. However, the use of rat, rabbit, and frog cells is also possible.

Alternatively, human somatic cells capable of producing antibody, specifically B lymphocytes, are suitable for fusion with myeloma cell lines. While B lymphocytes from biopsied spleens or lymph nodes of individuals may be used, the more easily accessible peripheral blood B lymphocytes are preferred. The lymphocytes may be derived from patients with diagnosed breast or other adenocarcinomas.

5.3. MYELOMA CELLS

Specialized myeloma cell lines have been developed from lymphocyte tumors for use in hybridoma-producing fusion procedures [G. Kohler and C. Milstein, Eur. J. Immunol. 6:511–519 (1976); M. Schulman et al., Nature 276:269–270 (1978)]. The cell lines have been developed for at least three reasons. The first is to facilitate the selection of fused hybridomas among unfused and similarly indefinitely self-propogating myeloma cells. Usually, this is accomplished by using myelomas with enzyme deficiencies that render them incapable of growing in certain selective media that support the growth of hybridomas. The second reason arises from the inherent ability of lymphocyte tumor cells to produce their own antibodies. The purpose of using monoclonal techniques is to obtain immortal fused hybrid cell lines that produce the desired single specific antibody genetically directed by the somatic cell component of the hybridoma. To eliminate the production of tumor cell antibodies by the hybridomas, myeloma cell lines incapable of producing light or heavy immunoglobulin chains or those deficient in antibody secretion mechanisms are used. A third reason for selection of these cell lines is for their suitability and efficiency for fusion.

Several myeloma cell lines may be used for the production of fused cell hybrids, including X63-Ag8, NSI-Ag4/1, MPC11-45.6TG1.7, X63-Ag8.653, Sp2/0-Ag14, FO, and S194/5XX0.BU.1, all derived from mice, 210.RCY3.Ag1.2.3 derived from rats and U-226AR, and GM1500GTGAL$_2$, derived from rats and U-226AR, and GM1500GTGAL$_2$, derived from humans. [G. J. Hammerling, U. Hammerling and J. F. Kearney (eds.), Monoclonal antibodies and T-cell hybridomas In J. L. Turk (ed.) Research Monographs in Immunology, Vol. 3, Elsevier/North Holland Biomedical Press, New York (1981) ].

5.4. FUSION

Methods for generating hybrids of antibody-producing spleen or lymph node cells and myeloma cells usually comprise mixing somatic cells with myeloma cells in a 2:1 proportion as in the example in Section 6.2. (though the proportion may vary from about 20:1 to about 1:1), respectively, in the presence of an agent or agents (chemical or electrical) that promote the fusion of cell membranes. It is often preferred that the same species of animal serve as the source of the somatic and myeloma cells used in the fusion procedure. Fusion methods have been described by Kohler and Milstein [Nature 256:495–497 (1975) and Eur. J. Immunol. 6:511–519 (1976)], and by Gefter et al. [Somatic Cell Genet. 3:231–236 (1977)]. The fusion-promoting agent used by those investigators were Sendai virus and polyethylene glycol (PEG), respectively. The fusion procedure of the example of the present invention is a modification of the method of Kohler and Milstein, supra.

5. 5. ISOLATION OF CLONES AND ANTIBODY DETECTION

Fusion procedures usually produce viable hybrids at very low frequency, about $1 \times 10^{-6}$ to $1 \times 10^{-8}$. Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium containing hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells can synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT madia are hybrids formed from myeloma and spleen cells.

To facilitate screening of antibody secreted by the hybrids and to prevent individual hybrids from overgrowing others, the mixture of fused myeloma and B lymphocytes is diluted in HAT medium and cultured in multiple wells of microtiter plates. In two to three weeks, when hybrid clones become visible microscopically, the supernatant fluid of the individual wells containing hybrid clones is assayed for specific antibody. The assay must be sensitive, simple and rapid. Assay techniques include radioimmunoassays, enzyme immunoassays, cytotoxicity assay, and plaque assays.

5.6. CELL PROPAGATION AND ANTIBODY PRODUCTION

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels; the culture medium, also containing high concentrations of a single specific monoclonal antibody, can be harvested by decantation, filtration or centrifugation.

5.7. IN VITRO DIAGNOSTIC USES FOR MONOCLONAL ANTIBODIES TO HUMAN BREAST CARCINOMA

5.7.1. IMMUNOHISTOLOGICAL AND IMMUNOCYTOLOGICAL APPLICATIONS

The monoclonal antibodies of this invention can be used as probes in detecting discrete antigens in human tumors. The expression or lack of expression of these antigens can provide clinically exploitable information which is not apparent after standard histopathological evaluations. It may thus be possible to correlate the immuno-phenotypes of individual tumors with various aspects of tumor behavior and responsiveness to certain types of therapies, thus establishing important classifications of prognosis.

Monoclonal antibodies produced by the hybridoma methodologies herein described can be used to detect potential breast carcinoma cells in histological and cytological specimens and in particular, to distinguish well-differentiated from poorly-differentiated tumors based on staining patterns and intensities. For instance, using the immunoperoxidase staining technique described in Section 6.8.1., it has been observed that the monoclonal antibodies of its invention stained an apical membrane-associated moiety in sections of benign lesions and well-differentiated adenocarcinomas of the breast; less-differentiated tumors however, generally exhibited a cytoplasmic staining pattern. While normal breast tissue also exhibited the surface staining pattern of benign and well-differentiated lesions,the intensity of staining was considerably less (See TABLE XI, Section 6.10.3.).

Another important in vitro diagnostic application of the monoclonal antibodies of this invention is the evaluation of adenocarcinomas other than breast. The antibody has been used to detect the epitope in adenocarcinomas of several histotypes including colon, ovary, uterus, pancreas and prostate, while the normal counterparts at these histological sites did not express the determinant. Thus, the novel monoclonal antibody detects an antigenic determinant in these adenocarcinomas which is tumor-associated. For example, no normal ovaries have displayed detectable levels of the epitope, whereas 15/15 ovarian carcinomas have expressed the determinant. Since the expression of this antigenic determinant appears to be associated with neoplastic development in the ovary, the monoclonal antibody may be a useful immunodiagnostic reagent for ovarian carcinomas. Other adenocarcinomas (gastric, jejunal, colonic, pancreatic, prostatic and bronchogenic) exhibited varying incidences of antigen expression. Since every adenocarcinoma specimen did not contain detectable levels of the determinant, the monoclonal antibody identifies antigenic differences which may be prognostically significant.

As an alternative to immunoperoxidase staining, immunofluorescent techniques can be used to examine human specimens with monoclonal antibodies to breast carcinoma. In a typical protocol, slides containing cryostat sections of frozen, unfixed tissue biopsy samples or cytological smears are air dried and incubated with the monoclonal antibody preparation in a humidified chamber at room temperature.

The slides are then layered with a preparation of antibody directed against the monoclonal antibody, usually some type of antimouse immunoglobulin if the monoclonal antibodies used are derived from the fusion of a mouse spleen lymphocyte and a mouse myeloma cell line. This antimouse immunoglobulin is tagged with a compound that fluoresces at a particular wavelength for instance rhodamine or fluorescein isothiocyanate. The staining pattern and intensities within the sample are then determined by fluorescent light microscopy and optionally photographically recorded.

5.7.2. IMMUNOSEROLOGICAL APPLICATIONS

The use of the monoclonal antibodies described herein can be extended to the screening of human biological fluids for the presence of the specific antigenic determinant recognized. In vitro immunoserological evaluation of sera withdrawn from patients thereby permits non-invasive diagnosis of cancers. By way of illustration, human fluids, such as pleural fluids or lymph, can be taken from a patient and assayed for the specific epitope, either as released antigen or membrane-bound on cells in the sample fluid, using the anti-breast carcinoma monoclonal antibodies in standard radioimmunoassays or enzyme-linked immunoassays known in the art. Human sera can also be taken from a patient and assayed using standard techniques known in the art for the presence of specific circulating antigen recognized by the monoclonal antibodies described herein. This assay provides a simple serodiagnostic test for breast cancer.

5.8. IN VIVO DIAGNOSTIC AND THERAPEUTIC USES FOR MONOCLONAL ANTIBODIES TO HUMAN BREAST CARCINOMA

5.8.1. TUMOR LOCALIZATION

The monoclonal antibodies of this invention are capable of targeting breast carcinoma cells in vivo. They can therefore be used in humans for tumor localization and for monitoring of metastases. For this application, it is preferable to use purified monoclonal antibodies. Purification of monoclonal antibodies for human administration by ammonium sulfate or sodium sulfate precipitation followed by dialysis against saline and filtration sterilization has been described by Miller et al. [In Hybridomas in Cancer Diagnosis and Therapy, (1982) supra, p. 134,] and by Dillman et al. [Id. at p.155] which are hereby incorporated by reference. Alternatively, immunoaffinity chromatography techniques may be used to purify the monoclonal antibodies.

The purified monoclonal antibodies can be labelled with radioactive compounds, for instance, radioactive iodine, and administered to a patient intravenously. After localization of the antibodies at the tumor or metastatic site, they can be detected by emission tomographical and radionuclear scanning techniques thereby pinpointing the location of the cancer. Experimental radioimmunodetection with monoclonal antibodies by external scintigraphy has been reported by Solter et al. [Id., at p. 241] hereby incorporated by reference.

5.8.2. PASSIVE IMMUNOTHERAPY FOR TREATMENT OF HUMAN CANCER

Because the monoclonal antibodies of this invention are capable of inducing rapid and significant volume reduction of established, progressively growing solid tumors associated with the human breast, they may be used in the treatment of human breast cancers, both in females and males, and possibly in the treatment of other adenocarcinomas, particularly ovarian cancer. By way of illustration, purified anti-breast carcinoma monoclonal antibody (see Section 5.8.1) is suspended in an appropriate carrier, e.g., saline, with or without human albumin, at an appropriate dosage and is administered to a patient. The monoclonal antibodies are preferably administered intravenously, e.g., by continuous intravenous infusion over several hours, as in Miller et al., incorporated by reference, supra. Infusions can be administered over a period weeks during which the antitumor effects are monitored.

The monoclonal antibodies described herein may be used clinically in conjunction with bone marrow transplantation or replacement therapies. Bone marrow tapped from patients undergoing treatment can be contacted with the anti-breast carcinoma monoclonal antibodies to eliminate contaminating cancer cells bearing the specific epitope by immunoadsorption. Cells may also be eliminated by complement mediated cytolytic procedures. Because the antigenic determinant recognized by the anti-breast carcinoma monoclonal antibody is absent on bone marrow stem cells and lymphoid cells, the monoclonal antibodies can effectively remove breast carcinoma cells from autologous or allogenic bone marrow prior to transplantation or reinfusion.

5.8.3. TREATMENT OF HUMAN CANCER WITH MONOCLONAL ANTIBODY CONJUGATES

The monoclonal antibodies of this invention can be used in conjunction with a broad spectrum of pharmaceutical or cytotoxic agents such as: radioactive compounds (e.g., $I^{125}$, $I^{131}$); agents which bind DNA, for instance, alkylating agents or various antibiotics (e.g., daunomycin, adriamycin, chlorambucil); antimetabolites such as methotrexate; agents which act on cell surfaces (e.g., venom phospholipases and microbial toxins); and protein synthesis inhibitors (e.g., diphtheria toxin and toxic plant proteins). [For reviews on the subject, see Bale et al., Cancer Research 40:2965–2972 (1980); Ghose and Blair, J. Natl. Cancer Inst. 61(3):657–676 (1978) Gregoriadis, Nature 265:407–411(1988); Gregoriadis, Pharmac. Ther. 10:103–108 (1980); Trouet et al., Recent Results Cancer Res. 75:229–235 (1980)]. Of particular importance are those agents capable of exerting toxic effects at the level of the cell surface, such as adriamycin [Tritton, T. R. and Yee, G., Science, 217:248–50 (1982)].

The methods used for binding the cytotoxic agents to the monoclonal antibody molecule can involve either non-covalent or covalent linkages. Since non-covalent bonds are more likely to be broken before the antibody complex reaches the target site, covalent linkages are preferred. For instance, carbodiimide can be used to link carboxy groups of the pharmaceutical agent to amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde which is then reacted with the antibody molecule. Attachment occurs via formation of a Schiff base with amino groups of the antibody molecule. Additionally, drugs with reactive sulfhydryl groups have been coupled to antibody molecules.

Similarly, glycosidic enzymes such as neuraminidase or α-mannosidase can be conjugated to the monoclonal antibodies.

Conjugated antibodies can be administered to patients, as in Section 5.8.2., to achieve enhanced tumoricidal effects through the cytotoxic action of the chemotherapeutic agents or the increased binding effect of the glycosidase (See Section 6.7.5).

5.9. ACTIVE IMMUNOTHERAPY FOR TREATMENT OF HUMAN CANCER

The physical identity of the purified antigen identified by the monoclonal antibodies of this invention also contribute to more effective treatment modalities based upon specific active immunotherapies. By way of illustration, purified ductal carcinoma antigen (DCA) is suspended in an appropriate carrier, e.g., saline, with or without human albumin at an appropriate dosage and is administered to a patient in a vaccine formulation. The antigen may act as an immunogen to elicit a host immune response for the prevention and/or control of tumor growth.

The monoclonal antibodies described herein may also be used to prepare anti-idiotype antibodies that react with the antigen recognized by the monoclonal antibody. The anti-idiotype antibodies can be used in a vaccine formulation for therapeutic treatment of breast cancer and other adenocarcinomas.

6. EXAMPLES

6.1. BREAST CELL LINES AND TISSUES

Breast carcinoma cell lines used included the following: MCF-7, derived from pleural effusion of scirrhous carcinoma [Soule, D. H. et al., J. Natl. Cancer Inst., 51:1409–1416(1973)]; SK-BR-3, derived from pleural effusion of adenocarcinoma [Fogh, J. and Trempe, G., New Human Tumor Cell Lines In: J. Fogh (ed.) Human Tumor Cells In Vitro, pp. 115–153, New York: Plenum Press (1975)]; BT-20, derived from primary carcinoma [Lasfargues, E. Y. and Ozzello, L., J. Natl. Cancer Inst. 21:1131–1147 (1958)] and MDA-MB-157, derived from pleural effusion of medullary carcinoma [Young, R. K. et al., In Vitro, 9:239–245 (1974)]. Each of the carcinomas is tumorigenic in nude mice. Cultures of apparently normal mammary cells used included: HBL-100, epithelial cells derived from a human milk sample [Polanowski, F. P. et al., In Vitro 12:328–336 (1976)] and HS0578 Bst, myoepithelial cells derived from normal tissue adjacent to primary carcinoma [Hackett, A. J. et al., J. Natl. Cancer Inst., 58:1795–1806 (1977)]. Neither normal breast cell line is capable of producing tumors in nude mice. Murine mammary tumor cell line MMT 060562 was obtained from the American Type Culture Collection.

Tissue specimens representing normal, benign, and malignant breast lesions, along with other tissues, were obtained from the Pathology Department of St. Joseph's Hospital, Buffalo, N.Y. All specimens were histopathologically assessed.

6.2. IMMUNIZATION AND CELL FUSION

Balb/c mice received, on days 0, 7 and 14, intraperitoneal injections ($5\times10^6$ cells per 0.2 ml) of live breast cancer cells which were suspended in Dulbecco's phosphate-buffered saline (D-PBS). On day 60, mice received an intravenous challenge of $2\times10^6$ cells in D-PBS. Cell fusion was carried out 3 days later according to the procedure developed by Kohler and Milstein [Nature (Lond.) 256:495–497 (1975)], with modifications: Balb/c mouse splenocytes ($1\times10^8$ cells) were fused in 0.15M HEPES (hydroxy-ethylpiperazine-ethanesulfonic acid) buffer (pH 7.5) comprising 40% (v/v) polyethylene glycol (PEG, MW=3,400) and 10% (v/v) dimethyl sulfoxide (DMSO) with 5×107 mouse myeloma cells (P3×63Ag8.653). Fused cells were distributed to 96-well culture dishes and cultured in selective hypoxanthine-aminopterin-thymidine (HAT) medium at 37° C. with 7.5% $CO_2$ in a humid atmosphere. Two to three weeks later, supernatants were assayed for direct binding activity on breast cancer cell lines. Hybridomas were detected in over 3,000 culture wells, with approximately 5% secreting antibodies reactive against MCF-7 breast cancer cells as determined by cell-surface radioimmunoassay (see Section 6.5.). Cultures showing specificity towards breast cancer were cloned by limiting dilution and subcloned in agarose [See e.g., Schreier, M. et al., Hybridoma Techniques, pp. 11–15, Cold Spring Harbor Laboratory, Cold Spring Harbor, N.Y. (1980)]. Stable cultures of antibody-producing hybridomas were expanded in complete media [RPMI-1640 media supplemented with 10% (w/v) heat-inactivated fetal bovine serum, 100 U/ml penicillin, 100 μg/ml streptomycin, and 10 μg/ml insulin (GIBCO Grand Island, N.Y.)] and exhausted culture fluids were the only source of antibodies used.

Following this procedure, hybridoma cell line F36/22, derived from immunization with MCF-7 cells, was obtained. The hybridoma was grown in mass culture in complete medium to produce monoclonal antibody for characterization studies and other applications described below.

6.3. ISOTYPING OF F36/22 MONOCLONAL ANTIBODIES

To determine the class of immunoglobulin produced by the F36/22 hybrid, $10^7$ F36/22 hybridoma cells were washed in D-PBS, collected by centrifugation and lysed in 100 μl of 0.5% Nonidet P-40 for 20 minutes on ice. Ten μl of the 40,000×g supernatant were examined by immunodiffusion against antisera specific for each of murine immunoglobulin classes: IgM, IgG1, IgG2a, IgG2b and IgG3 (Miles Laboratories, Elkhart, Ind.). Isotype analysis revealed that monoclonal antibody produced by F36/22 (hereinafter McAb F36/22 or monoclonal antibody F36/22) was an immunoglobulin of the γ3 class.

6.4. IMMUNOGLOBULIN PREPARATIONS

The monoclonal antibody F36/22 and control murine γ3 immunoglobulin were isolated in an identical manner using *Staphylococcal aureus* protein A-Sepharose (Pharmacia, Piscataway, N.J.) as described [Ey, P. L. et al., Immunochem., 15:429–36 (1978)]. Diluted serum or ascites or clarified culture fluid were applied to the protein A-Sepharose adsorbent followed by removal of non-binding components with pH 6.0 buffer. Immunoglobulin of the γ3 subclass was eluted at pH 4.5, neutralized with sodium hydroxide (NaOH) and dialyzed into PBS (phosphate buffered saline; 10 mM phosphate, pH 7.4). All immunoglobulin preparations were adjusted to 1 mg/ml and frozen in small aliquots until needed.

Immunoglobulin preparations used for the present studies were at least 95% pure as judged by polyacrylamide gel electrophoresis [Laemmli, U. K., Nature 227:680–85 (1970)].

6.5. CELL-SURFACE RADIOIMMUNOASSAY (CS-RIA)

Unless otherwise indicated, target cells were fixed in 2% p-formaldehyde/D-PBS for 10 minutes at room temperature and stored in the presence of assay buffer [D-PBS/0.1% gelatin/1 mM PMSF (phenyl methyl sulfonyl fluoride)/0.05% azide] at 4° C. for up to 2 weeks. To perform the assay, $1\times10^5$ cells were incubated with 100 μl of culture fluid from a culture of the F36/22 hybridoma for 2 hours at room temperature. Cells were washed 3 times with assay buffer before the addition of rabbit anti-mouse immunoglobulin diluted 1/500 in assay buffer [Brown, J. P. et al., J. Immunol. Methods 31:201–209 (1979)]. After 1 hour at room temperature, cells were washed and treated with $^{125}$I-labelled Staphylococcal Protein-A (Pharmacia, Piscataway, N.J.) at $2.5\times10^5$ cpm per dose. After ½ hour, the cells were washed, dissolved in 2N NaOH and transferred to tubes, where bound radioactivity was measured.

6.6. IN VITRO CHARACTERIZATION OF MONOCLONAL ANTIBODY F36/22

6.6.1. DETECTION AND BINDING OF McAb F36/22 TO CULTURED CELLS

McAb F36/22 was tested by CS-RIA against a panel of cell types (TABLE I). McAb F36/22 produced a strong reaction (greater than 10,000 cpm) against breast cancer cells MCF-7 and BT-20 and a significant reaction versus the other tested breast cancer lines. This-antibody weakly bound to a colon carcinoma and to a pancreas carcinoma (10 to 20% of maximum binding relative to MCF-7 cells). Other cells tested, including lymphoid/leukemoid cells, fibroblasts, and erythrocytes and cultures representing apparently normal mammary epithelial cells [Polanowski, F. P. et al. (1976), supra] and myoepithelial cells [Hackett, A. J. et al. (1977) supra] also failed to bind significant levels of antibody F36/22 (less than 10% of maximum binding). The results obtained from the cell surface binding assay, as summarized in TABLE I, indicate that the specificity recognized by McAb F36/22 is expressed maximally on selected breast cancer cells.

TABLE I

CELL-SURFACE BINDING OF ANTIBODY F36/22[a]

| Target Cell | % of maximum binding activity[b] F36/22 |
|---|---|
| Breast Carcinoma | |
| BT-20 | 99 |
| SK-BR-3 | 23 |
| MCF-7 | 100 |
| MDA-MB-157 | 44 |
| Mouse Mammary Tumor MMT 060562 | 5 |

TABLE I-continued

CELL-SURFACE BINDING OF ANTIBODY F36/22[a]

| Target Cell | % of maximum binding activity[b] F36/22 |
|---|---|
| Pancreas Carcinoma | |
| BxPC-3 | 8 |
| PANC-1 | 13 |
| Prostate Carcinoma | |
| LNCaP | 3 |
| PC-3 | 6 |
| Colon Carcinoma | |
| HT-29 | 16 |
| Lung Carcinoma | |
| PC3 | 4 |
| CHAGO | 5 |
| Rhabdomyosarcoma | |
| A-204 | 2 |
| Melanoma | |
| Palarmo | 3 |
| Thyroid Carcinoma | |
| TT-4 | 1 |
| Lymphoblastoid/Leukemoid | |
| RAJI (B-Cell) | 6 |
| DAUDI (B-Cell) | 8 |
| BALM-3 (B-Cell) | 5 |
| RPMI-6410 (B-Cell) | 9 |
| PEER (T-Cell) | 5 |
| MOLT-4 (T-Cell) | 4 |
| U-937 (monocytoid) | 9 |
| K-562 (erythroleukemoid) | 10 |
| Normal Breast | |
| HBL-100 (epithelial) | 2 |
| HSO578 Bst (myoepithelial) | 2 |
| Erythrocytes | |
| Type A | 3 |
| Type B | 5 |
| Type O | 4 |
| Type O (neuraminidase-digested)[c] | 3 |
| Fibroblasts | |
| BG-9 | 8 |
| Peripheral Blood Lymphocytes | 3 |

[a]Antibody binding activity was assessed by the cell-surface radioimmunoassay (CS-RIA).
[b]Maximum binding (100%) represents the cell line binding the most antibody, and binding to other cells was expressed relative to that level. The maximum cpm (mean of 2 experiments) was as follows: antibody F36/22; 10,743 cpm.
[c]Neuraminidase Digestion: Washed, type "O" erythrocytes were treated with C. perfringens neuraminidase (Boehringer-Mannheim, Indianapolis, IN) at 1 U enzyme/ml of 0.1M acetate/0.15M NaCl, pH 5.5. After 1 hour at 37° C., the cells were washed with CS-RIA assay buffer and assayed for antibody binding activity as compared to acetate buffer-treated control erythrocytes.

6.6.2. QUANTITATIVE ADSORPTION OF McAb F36/22 TO CULTURED CELLS

Adsorption tests were performed to determine if low binding levels obtained from the direct-binding assays presented in Section 6.6.1. were reflecting low levels of antigen, rather than absence of antigen. As shown previously [Dippold, W. G. et al., Proc. Natl. Acad. Sci. U.S.A., 77:6114–6118 (1980)], target cells tested against certain monoclonal antibodies may be direct-binding-testnegative/adsorption-test-positive. The number of cells required to adsorb 50% of antibody activity was calculated and presented as an $AD_{50}$ value according to the following procedure.

Suspensions containing different numbers of human cells ($10^3$ to greater than $10^7$ cells/ml) were added to equal volumes (total volume=200 μl) of hybridoma F36/22 culture supernatant fluid (approximately 38 ng murine IgG) and incubated for 1 hour on ice. The human cells used were: breast carcinoma BT-20, MCF-7, and MDA-MB-157; pancreas carcinoma PANC-1; colon carcinoma HT-29; lymphoblastoid RAJI; normal breast (epithelial) HBL-100; fibroblast BG-9; and red blood cells. After centrifugation, the binding activity remaining in the supernatant was measured using the CS-RIA.

Appropriate dilutions of hybridoma culture supernatant fluid were established by titration analysis of each antibody against breast cancer target cells. A final dilution of antibody was chosen which was midway down the slope, representing 50% of maximum binding activity. This corresponded to 38 ng antibody/ml final dilution for F36/22.

From the cpm of [$^{125}$I] Protein A bound to target cells, the estimated number of adsorbing cells required to remove 50% of the antibody activity was interpolated from a regression line of best fit.

The results of adsorption analyses indicated that the capacity to adsorb McAb F36/22 of the various cell types tested was greatest in selected breast cancer cells. Cultures of breast carcinoma cells BT-20, MCF-7 and MDA-MB-157 were able to adsorb F36/22 activity at $AD_{50}$ values of $3 \times 10^5$, $5 \times 10^5$, and $2 \times 10^7$, respectively. Fibroblasts and erythrocytes, along with lymphoblastoid, and colon carcinoma cells, showed no ability to adsorb McAb F36/22. Pancreas carcinoma cells demonstrated an $AD_{50}$ value of $1.6 \times 10^8$; this indicated very low levels of epitope F36/22, approximately 500-fold less than on BT-20 breast carcinoma.

6.6.3. RECIPROCAL BINDING INHIBITION

Reciprocal binding inhibition experiments were performed to determine whether McAb F36/22 recognized the same, closely associated or different antigenic determinants as antibodies to: fibronectin, human DR-antigen, α-fetoprotein, pregnancy-associated α-2-macroglobulin, carcinoembryonic antigen (CEA), class I HLA-A, B or C monomorphic determinants, β2-microglobulin or ferritin.

The procedure used to test reciprocal binding inhibition was as follows:

F36/22 hybridoma antibodies were internally labelled by the addition of 5 μCi of [$^{14}$C] leucine (New England Nuclear, Boston, Mass.) to cultures of $2 \times 10^6$ cells in 3 ml of leucine-free Modified Eagle's Medium (MEM) supplemented with 5% dialyzed fetal bovine serum. After 18 hours under standard culture conditions, culture fluids were clarified by centrifugation (20,000×g for ½ hour) and dialyzed against D-PBS/1 mM leucine/1 mM PMSF/0.05% azide. For competitive analysis, 50 μl of unlabelled antibodies (50-fold diluted sera or ascites) or 50 μl CS-RIA assay buffer (control) were allowed to react with target cells for 1 hour prior to the addition of $^{14}$C-labelled antibodies (50 μl). After 3 hours the cells were washed 4 times with CS-RIA assay buffer and counted. The 100% binding level was 2,200 cpm. Antibodies used for these studies included: anti-HLA monoclonal antibody W6/32 (Accurate Chemical Corp., Hicksville, N.Y.); anti-DR monoclonal antibody MAS-019 (Accurate Chemical Corp.); anti-CEA polyclonal antiserum [Chu, T. M. and Nemoto, T., J. Natl. Cancer Inst. 51:1119–1122 (1973)]; anti-α-fetoprotein polyclonal antiserum (obtained from H. Hirai, Hokkaido University, Japan); anti-pregnancy-associated macroglobulin (obtained from E.

J. Sarcione, Roswell Park Memorial Institute); anti-fibronectin monoclonal antibody MAS-037 (Accurate Chemical Corp.); anti-β2-microglobulin polyclonal antiserum (Accurate Chemical Corp.) and antiserum to human ferritin (obtained from E. J. Sarcione, Roswell Park Memorial Institute).

The per cent inhibition of McAb F36/22 binding activity by anti-CEA antibodies, anti-α-fetoprotein antibodies, and anti-β2-microglobulin antibodies was approximately 5% or less. The per cent inhibition by anti-fibronectin antibodies, anti-HLA antibodies, anti-DR-antigen antibodies, anti-pregnancy-associated macroglobulin antibodies, and anti-human ferritin antibodies was approximately 12% or less.

6.6.4. IN VITRO CYTOTOXICITY OF McAb F36/22

Complement-mediated cytotoxicity of monoclonal antibody was measured using the procedure of Brown et al. [J. Immunol. Methods, 30:23–35 (1979)]. Cells were incubated in the presence of McAb F36/22 plus rabbit complement for 1.5 hours after which time cells were evaluated for their ability to metabolically incorporate radioactive leucine as compared to untreated controls. Cells examined included Chago lung carcinoma [Rabson, A. S. et al., J. Natl. Cancer Inst., 50:660–74 (1973)], Daudi lymphoma [Klein, E. et al., Cancer Res., 28:1300–10 (1968)] and MCF-7 breast carcinoma [Soule, H. D. et al., J. Natl. Cancer Inst., 51:1409–16 (1973)].

Titration data summarized in TABLE II demonstrate that McAb F36/22 is cytotoxic to MCF-7 breast carcinoma cells in the presence of complement. This cytotoxic effect has been demonstrated at high dilutions of antibody. Also, the cytotoxicity observed is specific for antigen-expressing tumor cells. Cell lines expressing undetectable amounts of determinant, such as Chago lung carcinoma and Daudi lymphoma, were not significantly killed in the presence of complement plus McAb F36/22 at high dilutions which were cytotoxic to breast carcinoma.

TABLE II

IN VITRO CYTOTOXICITY OF McAb F36/22
Approx. % Cytotoxicity at Various Antibody Dilutions

| Cell Line | Dilutions | | | | | |
|---|---|---|---|---|---|---|
| | $10^0$ | $10^{-1}$ | $10^{-2}$ | $10^{-3}$ | $10^{-4}$ | $10^{-5}$ |
| MCF-7 | 65 | 60 | 65 | 25 | 10 | 0 |
| Chago | 55 | 0 | 0 | 0 | 0 | 0 |
| Daudi | 60 | 0 | 0 | 0 | 0 | 0 |

In vitro antibody mediated complement cytotoxicity assays were repeated on BT-20 and MCF-7 cell lines. The results showed specific cell lysis (greater than 50% cell kill) at a concentration of 1 ng of McAb F36/22 per ml of medium and no cytolysis of 11 different non-breast cell lines (8 leukemia, 2 carcinomas, 1 lymphoma) at a concentration of 2.5 µg/ml. Rabbit or human complement at 1:10 dilution were both shown to be equally effective. Antibody without complement gave no significant cytolysis.

The rapidity of the tumoricidal process (see Section 6.9.3.) and the in vitro indication of specific cytolysis at very low concentration of McAb F36/22 with complement point to the involvement of a complement mediated effect. It has been reported that murine γ3 antibodies bind with low affinity and low frequency to murine macrophages [Ralph, P. et al., J. Immunol 125:1885–1888 (1980)]. The possibility exists, however, that antibody mediated cellular cytotoxicity also takes place.

6.6.5. REACTIVITY OF McAb F36/22 WITH ESTROPHILIN COMPLEXES

Experiments were performed to define the possible role of estrophilin in the reaction of McAb F36/22 against human breast carcinomas. Using an immunochemical assay, McAb F36/22 added prior to labelled estradiol was unable to competitively inhibit the formation of estradiol-estrophilin complexes. However, the possibility existed that even through F36/22 did not react with an epitope involved in the hormone-receptor binding site, it may detect an epitope located elsewhere on the estrophilin molecule. To evaluate this, the following procedure was used.

Radiolabelled estradiol-estrophilin complexes were prepared using MCF-7 cytosol as described by Horwitz and McGuire [Cancer Res. 37:1733–1738 (1977)], except that $^{125}$I-labelled estradiol was used (New England Nuclear, 2000 µCi/mM) in place of the tritiated reagent. Preformed complexes were incubated at 4° C. for 1 hour with McAb F36/22 (25 µg) or control immunoglobulin (25 µg) from serum of a non-immunized mouse as described previously [Greene, G. L. et al., Proc. Natl. Acad. Sci. U.S.A. 77:5115–5119 (1980)]. Each mixture was individually applied to a column (1×45 cm) packed with S-200 chromatography media and equilibrated with running buffer (10 mM Tris-HCl, pH 7.4 containing 1.5 mM DTT (dithiothreitol), 1 mM EDTA (ethylenediaminetetraacetic acid) and 400 mM KCl). Successive 1 ml fractions were collected and radioactivity was measured. Purified human hemoglobin (Sigma) was used as an internal marker of the 4S protein peak.

The estradiol-estrophilin complexes eluted in the 4S region both in the presence and absence of McAb F36/22 as compared to monoclonal antibodies which react with estrophilin [Greene, G. L. et al. (1980), supra], thus indicating no reactivity with the estrophilin molecule.

6.6.6. RELATIONSHIP BETWEEN ESTRADIOL CONCENTRATION AND McAb F36/22 BINDING LEVELS

Hormonal involvement of antigen expression in MCF-7 breast cancer was investigated. A study was performed to ascertain if increased antigen expression of estrogen receptor-rich (ER-rich) tumors was related to the estradiol concentration.

First, endogenous estradiol was removed from fetal bovine serum (FBS) used in normal complete cell culture medium. The basic procedure used was reported earlier by Westley and Rochefort [Cell 20:353–362 (1980)]. Fifty ml of FBS #309 (GIBCO) was depleted of estrogen as follows: A DCC suspension (0.025% Norit A and 0.0025% dextran in TESH (10 mM Tris-HCl, pH 7.4, containing 1 mM EDTA and 1.5 mM DDT buffer) was prepared according to the method of Garola and McGuire [Cancer Res. 38:2216–2220 (1978)]. The DCC (250 mg charcoal, 25 mg of dextran per 50 ml of FBS) was added to the FBS and mixed on an aliquot shaker at 55° C. for 30 minutes. After 2 treatments with DCC, the steroid-depleted FBS was sterile filtered through 0.2 µm Nalgene filters. Complete medium consisted of RPMI-1640 containing 10% estrogen-depleted FBS, 100 U/ml penicillin and 100 µg/ml streptomycin. All tissue culture reagents were obtained from GIBCO, Grand Island, N.Y.

The following protocol was used to determine the effect of exogenous estradiol on antibody binding levels. MCF-7 cells were washed twice in D-PBS, resuspended in steroid-depleted medium, and lightly seeded into replicate flasks. The medium was replaced every third day. On day 10, various final concentrations of estradiol-17 β-cypionate (Sigma) (0, $10^{-3}$, $10^{-6}$, $10^{-9}$M) in DCC-treated medium were added to the flasks. After 72 hours of stimulation, the cells were harvested by gentle aspiration, counted using a hemocytometer and aliquoted. Cells were washed twice in D-PBS and then fixed for 10 minutes in 2% p-formaldehyde in 30 mM phosphate buffer, pH 7.2. The cells were again washed and treated with 0.5% saponin in 30 mM phosphate buffer, pH 7.2, for 3 minutes to reveal intracellular binding sites [Fambrough, D. M. and Devreotes, P. N., J. Cell. Biol., 76:237–244 (1978)]. The cells were further washed and incubated with [$^{125}$I]-F(ab')$_2$ fragments of McAb F36/22 for 60 minutes (200,000 cpm/tube), washed 4 times, and the counts were measured in a Packard gamma spectrometer.

Competitive inhibition, using saturating doses (10 μg/sample) of unlabelled McAb F36/22 prior to the addition of the labeled F(ab')$_2$ fragments permitted an estimation of non-specific background. In addition, an irrelevant IgG3 control antibody (10 μg/sample) was incubated prior to the labelled fragments of McAb F36/22, in order to assess the specificity of the binding reaction.

Using these in vitro conditions, exogenous estradiol concentrations of $10^{-3}$ and $10^{-6}$M were shown to significantly increase the amount of antibody binding levels as compared to control-treated cultures (p less than 0.001) (TABLE III). Fixation of the MCF-7 cells with p-formaldehyde alone failed to elicit any significant changes in cell-surface binding in response to increasing concentrations of estradiol. However, treatment of the cells with saponin, which reveals intra-cytoplasmic binding sites, greatly promoted the binding of McAb F36/22. This in vitro observation coincides with the in vivo tumor staining patterns (see Section 6.9.), where the predominant location of immunoperoxidase staining in ER-rich tumors is cytoplasmic (80%).

TABLE III

RELATIONSHIP BETWEEN ESTRADIOL LEVELS
AND ANTIGEN EXPRESSION OF MCF-7 CELLS[a]

| Final Estradiol Concentration | [$^{125}$I]-F(ab')$_2$ cmp bound/ $10^5$ MCF-7 Cells[b] |
|---|---|
| 0 | 3975 ± 556 |
| $10^{-9}$M | 4213 ± 842[c] |
| $10^{-6}$M | 5333 ± 640[d] |
| $10^{-3}$M | 6133 ± 306[d] |

[a]MCF-7 cells, maintained in estrogen-depleted medium for 10 days, were stimulated with various final concentrations of estradiol. After 72 hours, the cells were harvested, counted and aliquoted into 3 tubes/flask. The cells were fixed in buffered 2% p-formaldehyde for 10 minutes, and further treated with 0.5% buffered-saponin for 3 minutes to reveal intracellular binding sites. The cells were then incubated with [$^{125}$I]-F(ab')$_2$ fragments of McAb F36/22 for 60 minutes (200,000 cpm/tube), and the counts bound were measured in a gamma spectrometer.
[b]In this experiment, specific binding of McAb F36/22 fragments was calculated by subtracting the non-specific binding in the presence of saturating levels of unlabelled McAb F36/22 from the total counts bound. Results were expressed as [$^{125}$I]-F(ab')$_2$ cpm bound/$10^5$ MCF-7 cells.
[c]Not statistically significant.
[d]Statistically significant antibody binding (p less than 0.05) as compared to control treated cultures (Student's t test).

Because exogenous estradiol was capable of increasing the cytoplasmic binding of McAb F36/22 to saponin-treated MCF cells, the antigen which McAb F36/22 recognizes may represent a protein whose synthesis is regulated under the estrogen-response machinery of the breast cancer cell. The existence of several estrogen-regulated proteins has been well established [see e.g., Butler, W. B. et al., Biochem. Biophys. Res. Commun., 90:1328–1334 (1979); and Capany, F. et al., Biochem. Biophys. Res. Commun., 108:8–15 (1982)] and monoclonal antibodies to estrogen-receptor status-related components have been described [Ciocca, D. R. et al., Cancer Res., 42:4256–4258 (1982)]. Identification of such proteins may add new information regarding hormonally-dependent regulatory controls involved in breast cancer which may ultimately lead to new therapies.

6.7. CHARACTERIZATION OF THE ANTIGEN RECOGNIZED BY MONOCLONAL ANTIBODY F36/22

6.7.1. SOLID-PHASE ADSORPTION OF BT-20 BREAST CARCINOMA ANTIGEN BY LECTINS

The following solid-phase ligands were tested for their capacity to react with antigen occurring in BT-20 breast cancer cell lysates: Concanavalin A-Sepharose CL-4B (Pharmacia), in 50 mM sodium acetate/1M NaCl/1 mM CaCl$_2$/1 mM MnCl$_2$, pH 6.0 (binding capacity 8.5 mg/ml gel); Wheat-germ Sepharose 6MB (Pharmacia), in D-PBS (binding capacity 5 mg/ml; Peanut Agglutinin-Ultrogel (LKB, Rockville, Md.), in D-PBS (binding capacity 4 mg/ml); and Gelatin-Agarose (BioRad, Richmond, Calif.), in D-PBS (binding capacity 6 mg/ml).

Samples of BT-20 breast cancer cell lysates (8 mg protein/ml) were prepared in D-PBS/0.5% sodium deoxycholate and were incubated with an equal volume of solid-phase ligand (25% v/v suspension in the appropriate buffer). After 1 hour at 4° C., the beads were washed 3 times and incubated with F36/22 hybridoma culture fluid for 2 hours at 4° C. Subsequently, antibody binding activity was revealed using the CS-RIA (Section 6.5.) procedure as for target cells. Since standard preparations of purified BT-20 breast cancer antigen was not available in this set of experiments as reference material, results of these assays were used to obtain qualitative information regarding lectin binding activities.

Concanavalin A was able to bind soluble components from BT-20 breast cancer cell lysates which in turn exhibited the capacity to adsorb McAb F36/22. Peanut agglutinin and wheat germ lectins had a more limited ability to bind F36/22 antibody-reactive components from BT-20 cell lysates (less than 20% of that exhibited by concanavalin). Also tested was insolubilized gelatin, which produced no antibody binding activity after treatment with breast cancer cell lysates.

6.7.2. ANTIGEN MODULATION

The stability of cell surface antigen after treatment of MCF-7 cells with McAb F36/22 was investigated.

To sensitive viable MCF-7 breast carcinoma cells growing in microwell plates, the cells were allowed to incubate in the presence of saturating doses of monoclonal antibody (10 μg/ml of sterile complete medium). The experiment was run at 0°, 23° and 37° C. At successive time intervals up to 4 hours the cells were washed and assayed for McAb F36/22 binding as described in Section 6.5. Additionally, monoclonal antibody-sensitized cells were also examined under immunofluorescence using fluorescent labelled antibody (where the fluorescent label was fluorescein isothiocyanate (FITC)) against murine immunoglobulin (Accurate Chemical Co., Hicksville, N.Y.) [see Papsidero, L. D. et al. Hybridoma, 1:275–82 (1982)].

No loss of McAb F36/22 binding levels was noted after 4 hours even at the highest temperature tested, 37° C. This indicated no external modulation or redistribution of McAb F36/22-complexed cell surface antigen. Immunofluorescence examination of identically-treated cells showed the presence of strong staining which was limited to the cell surface.

6.7.3. RELEASE OF ANTIGEN RECOGNIZED BY McAb F36/22 BY TUMOR CELLS

To examine if antigen recognized by McAb F36/22 was spontaneously released by tumor cells, pleural fluids were examined using a nitrocellulose direct-binding assay procedure. These fluids were obtained from patients with disseminated breast carcinoma and were histopathologically evaluated for the presence of tumor cells.

Detection of antigen which was adsorbed to nitrocellulose paper was performed using an antigen spot test as described by Herbrink et al. [J. Immunol. Methods 48:293–8 (1982)]. Briefly, antigen samples in the form of pleural fluids (or chromatography fractions as described in Section 6.7.4.) were applied as 10 µl drops to nitrocellulose transfer paper (BioRad, Richmond, Calif.) and allowed to dry for 15 minutes Thereafter the paper was inactivated by incubation in assay buffer (0.1M Tris-HCl, pH 7.4 containing 0.25% (w/v) gelatin and 0.5% (v/v) nonidet P40). The paper was then incubated for 18 hours at 4° C. with antibody F36/22 at 10 µg/ml of complete culture medium. After washing the paper 4 times with assay buffer, the bound antibody was detected by incubating the paper with $^{125}$I-labelled goat F(ab')$_2$ antibodies to murine immunoglobulin [Fraker, P. J. and Speck, Jr., J. C., Biochem. Biophys. Res. Commun., 80:849–57 (1978)]. After washing, the paper was sectioned and individual samples counted for bound radioactivity.

To avoid spurious binding to human immunoglobulins, the radiolabelled anti-murine antibody was affinity-purified on murine immunoglobulin-Sepharose columns and further adsorbed with solid-phase human immunoglobulins [March, S. C. et al., Anal. Biochem. 60:149–52 (1974)]. The resulting antibody preparation demonstrated less than 1% cross-reactivity against purified human IgG.

When compared to normal serum donors, the malignant effusions tested exhibited an increased level of McAb F36/22 binding activity and increased incidence of elevated antigen amounts (p less than 0.02); 9 out of 10 samples derived from healthy blood serum donors bound less than or equal to 3923 cpm while 17 out of 24 pleural fluid samples from breast carcinoma patients exhibited binding of 3923 cpm or more, with one sample binding as high as 1×10$^5$ cpm. Also, when control murine immunoglobulin was substituted for McAb F36/22, no difference was observed between normal donors and cancer patients, indicating immunological specificity for the reaction.

Though physicochemical characterization of the pleural effusion-borne antigen(s) carrying the specific epitope recognized by McAb F36/22 were not performed as in Section 6.7.4., the results of the antigen spot test suggest serological applications for McAb F36/22 as described below.

6.7.4. GEL FILTRATION CHROMATOGRAPHY OF MCF-7 ANTIGEN RECOGNIZED BY McAb F36/22

MCF-7 primary breast carcinoma cells were homogenized at 4° C. in detergent buffer (10 mM Tris, pH 7.4/0.5% (w/v) sodium deoxycholate/0.5 mM phenylmethylsulfonyl fluoride). Nuclei and debris were removed by centrifugation at 40.000×g for 1 hour. Five ml of the clear supernatant were applied to a column (2.6×100 cm) packed with Sephacryl S-300 gel filtration media (Pharmacia) and equilibrated with the above detergent buffer. The column was run at a flow rate of 15 ml/hr and fractions of 5 ml were collected. The column was pre-calibrated using protein markers of known molecular weight |thyroglobulin (19.2 s), immunoglobulin G (7 s), and serum albumin (4.5 s)|.

Fractions collected were individually tested for their immunoreactivity against monoclonal antibody F36/22 using the antigen spot test (see Section 6.7.3.). As control, the test was also performed using P3×63-Ag8 immunoglobulin as a substitute for specific antibody. Fractions eluting at approximately 5 s demonstrated significant reactivity against McAb F36/22. These fractions showed no such reactivity versus control immunoglobulin.

6.7.5. EFFECT OF ENZYME DIGESTIONS ON CELL SURFACE ANTIGENICITY

Breast carcinoma cells (MCF-7) at a concentration of 1×10$^6$ cells/ml were subjected to the following reagents (final concentration) at 37° C.: Papain (Boehringer-Mannheim, Indianapolis, Ind.) at 0.8 U/ml in pH 6.3 PBS containing 1 mM cysteine and 1 mM EDTA; Trypsin (GIBCO) at 1372 U/ml of Hank's salt solution containing 0.5 mM EDTA; Pepsin (Sigma, St. Louis, Mich.) at 243 U/ml of acetate buffer pH 4.5; Neuraminidase (Boehringer-Mannheim) at 0.05 U/ml of acetate buffer pH 5.0 containing 1 mM phenylmethyl sulfonyl fluoride; α-mannosidase (Sigma) at 1 U/ml of acetate buffer, pH 4.5 containing 1 mM ZnCl; Sodium-meta-periodate (Sigma) at 50 mM in PBS.

Cells were incubated with proteolytic enzymes for 5 minutes while the incubations with carbohydrate-cleaving agents were allowed to continue for 30 minutes. Cell viability was greater than 85% after each of these treatments. Subsequently, the cells were washed and assayed for residual antigenicity by direct-binding CS-RIA as described in Section 6.5. using monoclonal antibody F36/22.

The cell surface component recognized by F36/22 was labile under proteolytic conditions and resisted carbohydrate-cleaving reagents.

Direct binding of McAb F36/22 to breast carcinoma cells, and hence, cell-surface antigenicity was significantly diminished after treatment of the cells with papain and trypsin. Papain digestion and trypsin digestion reduced direct binding activity to approximately 40% and 10% of control values, respectively. Treatment with pepsin showed no effect on direct binding. All carbohydrate-cleaving agents tested produced a dramatic increase in antibody binding activity: Neuraminidase, α-mannosidase and periodate increased direct binding by 200%, 250% and 400% of control values, respectively. This effect was not based upon cellular uptake of the antibody reagents, as in each case greater than 85% viability of the cells was observed post-treatment.

The reason for the dramatic increase in antigenicity following treatment with carbohydrate-active reagents such as periodate and glycosidases may be that these reagents clear and/or "unmask" the cell surface of some carbohydrate moieties thus allowing greater access of McAb F36/22 to determinants directly adjacent to the cell membrane.

6.8. DETECTION OF DUCTAL CARCINOMA ANTIGEN IN BREAST CANCER SERA USING MONOCLONAL ANTIBODY F36/22

A quantitative immunoassay procedure was constructed to evaluate levels of the ductal carcinoma antigen (DCA) recognized by McAb F36/22 in a human fluid sample. The cell-surface component(s) is associated with a line of epithelial tumors of ductular lineage.

6.8.1. ENZYME IMMUNOASSAY PROCEDURE

The sandwich type of enzyme immunoassay was developed based upon observations presented below (Sec. 6.9.4. and 6.9.5.) which indicated the occurrence of multiple antibody combining sites on DCA.

To develop the procedure, antigen standards comprising a papain digest of breast tumor specimens (shown to contain the antigen by immunoperoxidase staining) were used. Human primary breast cancer specimens were pooled and homogenized in 10 volumes of 10 mM Tris buffer, pH 7.4, containing 0.2% (w/v) sodium deoxycholate at 4° C. The homogenate was quickly brought to 37° C. and the following reagents (final concentration) were added while stirring: 1 mM cysteine (Sigma), 1 mM EDTA (Sigma), and papain (0.8 unit/ml) (Boehringer-Mannheim, Indianapolis, Ind.). After 5 minutes digestion was stopped by the addition of 5 mM iodoacetamide (Sigma). The homogenate was centrifuged at 100,000×g for 1 hour at 4° C., then extensively dialyzed against 10 mM Tris/0.9% NaCl solution buffer, pH 7.4, containing phenylmethysulfonyl fluoride and aminocaproic acid, each at 10 mM. The homogenate was frozen in small aliquots at a concentration of 0.5 mg of protein/ml. Polyacrylamide gel electrophoresis of the papain digest revealed the presence of several major glycoproteins.

The dose response curve generated for the immunoassay procedure measuring DCA demonstrated linearty (r=0.98, linear regression analysis) between antigen input of 0.625 to 10 units/ml. For serum analysis, the range was 16.25 to 260 units/ml, since these samples were diluted 26-fold prior to assay. The values of antigen content were arbitrarily assigned in the absence of purified antigen during development of the assay.

Solid-phase preparations of McAbs were prepared using CNBr-activated Sepharose (Pharmacia). Microtiter plates (Nunc I Immunoplates; Grand Island Biological Co., Grand Island, N.Y.) were coated with McAbs (200 µl/well) in 50 mM carbonate-bicarbonate buffer, pH 9.6, for 18 hours at 4° C. After removal of the antibody solution, residual protein binding sites on the plastic were blocked by the addition of 200 µl of assay buffer [PBS containing 1% (v/v) murine serum and 1% (w/v) bovine albumin]. After 1 hour of incubation at room temperature, the coated plates were used immediately for the assay procedure.

To perform the assay, 200 µl (10 units/ml) samples, diluted in assay buffer, were applied for 1.5 hours at 37° C. After 3 washes using assay buffer, 200 µl of McAb F36/22 covalently conjugated to horseradish peroxidase (Sigma, Type VI) was applied to each well for 1.5 hours at 37° C. The conjugate was diluted to a concentration of 0.5 µg of immunoglobulin per ml of PBS containing 10% (v/v) murine serum. Following a wash procedure as above, 200 µl of substrate per well were applied for 0.5 hours at room temperature. Substrate solution contained 0.4 mg of o-phenylenediamine per ml of pH 5.0 citrate buffer and 0.003% hydrogen peroxide. The reaction was stopped by addition of 50 µl of 2N sulfuric acid, and absorbance was monitored at 488 nM using an enzyme assay plate reader (Fisher Scientific Co., Pittsburgh, Pa.).

The percentage of bound enzyme conjugate was calculated by the formula:

$(B-B_0)/(B_r-B_0) \times 100$ where B=absorbance of the sample, $B_r$=maximal absorbance, and $B_0$=absorbance of the blank. Each assay was performed in triplicate using a standard papain digest and 26-fold diluted serum samples diluted in assay buffer. Samples producing an absorbance corresponding to greater than 50% bound were serially diluted and reassayed. Samples showing a standard deviation above 10% were also reassayed. An interassay coefficient of variation of 12% was observed for 14 consecutive assays.

Specificity of the immunoassay was examined by substituting various antibody reagents at the solid phase, including McAb F5 (prostate antigen specific [Papsidero, Hybridoma 2:139-147 (1983)]; McAb M7/105, distinct tumor antigen specific [Papsidero et al., Cancer Res. 43:1741-1747 (1983)]; and nonimmune murine serum. Of the solid phase antibodies only antibody F36/22 bound antigen at high dilutions.

Levels of serum ductal carcinoma antigen were detected for normal controls subjects, patients with benign and malignant breast diseases and patients with prostatic and gastrointestinal cancer.

Sera obtained from 64 apparently healthy individuals exhibited a mean value of approximately 28 units of DCA/ml. Only 3% of the samples expressed serum antigen at 70 units/ml or above, and this value was arbitrarily chosen as cutoff for elevated serum levels. This group, in addition to laboratory personnel, contained 32 samples obtained from age-matched controls (Table IV). No statistically significant difference was observed between these groups regarding circulating DCA levels. Furthermore, long-term (1 year or greater) storage of sera or 3 cycles of freeze-thaw failed to significantly alter DCA values. Similar values were obtained using freshly drawn and unfrozen sera from 10 volunteers (mean value, 29 units/ml). All sera to be evaluated were diluted 26-fold prior to assay, as based upon antigen recovery experiments. At dilutions below 20-fold, the recovery of antigenic activity was less than 100% and a source of experimental underestimate of DCA levels.

Sera from patients with benign disease of the breast (most with fibrocystic disease) exhibited a mean DCA value of 41.5 units/ml (Table IV). The incidence of values above 70 units/ml was 13% (5 of 40 specimens). Patients with breast cancer (with evidence of disease) exhibited a wide range of circulating levels of DCA with a mean value above 700 units/ml. The incidence of elevated values for this group was approximately 53% (61 out of 116 specimens). Patients with early stage disease or with no clinical evidence of disease demonstrated a decreased incidence of elevated serum antigen values (Table IV). Approximately 30% of these specimens contained levels of DCA above 70 units/ml.

TABLE IV

DETECTION OF DUCTAL CARCINOMA ANTIGEN IN SERUM

| | | Antigen level (units/ml) | |
|---|---|---|---|
| Group | No. tested | Mean | >70 units/ml (%) |
| Apparently healthy controls | | | |
| Lab personnel | 32 | 28.9 ± 18.2[a] | 1 (3) |
| Age-matched | 32 | 27.9 ± 16.3 | 1 (3) |
| Patients with benign breast disease | 40 | 41.5 ± 43.2 | 5 (13) |
| Patients with non-breast cancer | | | |
| Prostate | 65 | 28.3 ± 24.8 | 7 (11) |
| Miscellaneous gastrointestinal | 112 | 60.2 ± 50.4[b] | 30 (27) |

TABLE IV-continued

DETECTION OF DUCTAL CARCINOMA ANTIGEN IN SERUM

| Group | No. tested | Antigen level (units/ml) Mean | >70 units/ml (%) |
|---|---|---|---|
| Patients with breast cancer | | | |
| Early stage | 15 | 49.9 ± 23.7[b] | 5 (33) |
| Late stage (ED[c]) | 101 | 719.1 ± 3446.2[b] | 56 (56) |
| Late stage (NED) | 15 | 52.9 ± 22.8[b] | 4 (27) |

[a]Mean ± S.D.
[b]$p < 0.05$ as compared to control population (Student's t test analysis).
[c]ED, patients with clinically detectable evidence of disease; NED, no evidence of clinically detectable disease.

Serum samples were also obtained from 12 patients prior to and 4 days after mastectomy in order to evaluate the response of serum antigen levels to surgery. Of these 12 patients, 4 showed pretreatment levels greater than 70 units/ml. After surgery, each patient in this latter group demonstrated a decrease in serum DCA level to the normal range (Table V).

TABLE V

ANALYSIS OF ANTIGEN LEVEL PRIOR TO AND AFTER MASTECTOMY

| Patient | Antigen level (units/ml) Presurgery | Postsurgery[a] |
|---|---|---|
| 361 | 82.7 | 38.4 |
| 347 | 73.3 | 19.2 |
| 283 | 90.7 | 68.9 |
| 269 | 71.8 | 43.3 |

[a]Sera obtained 4 days postsurgically. In each case shown, specimens obtained after treatment demonstrated significantly reduced antigen levels ($p < 0.001$).

Sera obtained from 65 patients with prostatic cancer and 112 patients with gastrointestinal cancer (advanced disease) were evaluated (Table IV). The incidence of elevated DCA values was 11 and 27%, respectively. Mean serum values from the group with gastrointestinal cancer (60 units/ml) were significantly higher than control levels.

All human sera examined also showed detectable levels of antigen activity. The source of antigen, as occurring in the circulation of normal individuals, is not known. Since a few normal ductal epithelia structures have been shown to express antigen, their contribution is circulating immunoreactivity appears probable. However, the quantitative range of antigen levels in the normal serum controls is narrow and may be discriminated from specimens of patients' sera.

The highest incidence and levels of circulating DCA were associated with patients with clinical evidence of breast cancer. The incidence of elevated serum levels in this group (approximately 50%) may be based upon the observations described in Section 6.10. which indicated that only a subset of breast tumors expresses antigen. Since the use of McAbs is associated with the description of intertumoral antigenic heterogeneity, this observed incidence is not surprising. There also appears to be, a strong correlation between the incidence of serum DCA levels and intratumoral expression of antigen. Tumor histotypes such as breast cancer, which exhibit a high incidence of tumor antigen, also show a related incidence of elevated circulating DCA values. These data predict that patients with mesenchymally derived tumors may present with low frequencies of circulating DCA.

Of clinical importance, these data also suggest that patients with ovarian ductal carcinomas may exhibit a high incidence of DCA serum elevations. As shown in Table V 100% of such tumors express antigen and may potentially be diagnosed by serodetection. In any event, differential diagnosis of ductal carcinomas, as based upon serum values, may be facilitated in a manner analogous to our studies performed using solid tumor specimens.

Using a limited number of mastectomy patients with primary localized disease, a significant decrease in serum DCA occurred postoperatively. These data indirectly indicate a relationship between serum DCA levels and tumor load, suggesting that such measurements may be of value for patient monitoring. Perhaps equally important, is the fact that DCA values in no instance were seen to increase postsurgically. This directly implies that the antigen under measurement does not represent a nonspecific "acute-phase reactant", the levels of which sharply increase following surgical therapy.

6.8.2. BIOCHEMICAL CHARACTERISTICS OF CIRCULATING SERA

Serum samples (0.5 ml) from 5 patients with breast cancer were subjected to size fractionation. Samples were filtered over a column (1.6×90 cm) packed with Sephacryl S-400 (Pharmacia). Column fractions eluted with PBS were diluted in enzyme assay buffer (PBS containing 1% (v/v) murine serum and 1% (w/v) bovine albumin) and evaluated for antigen activity. The column was pre-calibrated using protein standards of known molecular weight, including bovine thyroglobulin, aldolase, catalase, and albumin (Sigma).

Column fractions exhibiting peak antigen activity were further fractionated under equilibrium density gradient ultracentrifugation. Samples in PBS were brought to a density of 1.45 g of cesium chloride per ml. After centrifugation ($1.5 \times 10^6 \times g$ for 72 hours at 10° C.), fractions were assayed for antigen activity and for density using an analytical balance.

Fractions obtained were evaluated for immunoreactivity using the enzyme immunoassay procedure.

Results demonstrated the presence of antigen activity eluting in high-molecular weight fractions ahead of the 669.000 molecular weight protein. Results were similar among the specimens examined. The density of the serum antigen was evaluated using equilibrium ultracentrifugation in the presence of cesium chloride and exhibited a peak at approximately 1.45 g/ml, although a broad range of activity was observed.

6.8.3. SOLID PHASE ADSORPTION OF SERUM ANTIGEN

The ability of serum antigen to interact with various solid phase-adsorbents also was studied. Serum specimens obtained from patients with breast cancer were incubated with the following solid-phase adsorbents (Sigma): (a) concanvalin A:Sepharose; (b) wheat germ:Sepharose; (c) peanut agglutinin; (d) lentil lectin:Sepharose; and (e) Protein A:Sepharose. Sepharose adsorbents derivatized with McAbs F36/22 and F5 were prepared using cyanogen bromide-activated Sepharose according to recommendations from the manufacturer (Pharmacia). Nonderivatized Sepharose served as a negative control (See also Sec. 6.9.6).

For adsorption studies, serum dilutions were incubated with adsorbents (50%, v/v) at a volume ratio of 1:40 for 18 hours at 4° C. All tests were performed in triplicate. After centrifugation (500×g), the supernatant was assayed for antigen activity.

Statistical evaluations (Student's t test) indicated that the solid-phase adsorbents prepared from wheat germ lectin and McAb F36/22 bound statistically significant (p less than 0.01) amounts of serum antigen as compared to control Sepharose.

As seen in FIG. 1, the significant amount of antigen bound by immobilized wheat germ lectin indicated the presence of available β-N-acetylglucosaminyl groups. The specificity of this interaction was confirmed by competitive inhibition using β-N-acetylglucosamine (100 ng/ml). Negligible binding to Protein A: Sepharose suggested the absence of circulating immune complexes. Significant amounts of antigen were not observed to react with other lectins, including concanavalin A, lentil lectin, and peanut agglutinin.

6.9. IMMUNOAFFINITY ISOLATION OF DUCTAL CARCINOMA ANTIGEN USING MONOCLONAL ANTIBODY F36/22

McAb F36/22 recognizes a mucin-like glycoprotein occurring in malignant effusions and in human sera. Mucins or mucoproteins are a class of glycoproteins in which acid mucopolysaccharides, usually containing two types of alternating monosaccharide units of which at least one has an acid group, are complexed with specific proteins. Characteristics of the purified component appear distinct from previously described circulating antigens of breast and ovarian cancer. The data also indicate that mucins may carry tumor-related determinants.

Purification of antigen from the circulation of cancer patients was achieved through the use of sequential affinity chromatography steps based upon antigen interaction with McAb F36/22 and wheat germ lectin.

6.9.1. PURIFICATION OF ANTIGEN

The antigen recognized by McAb F36/22 was purified from malignant effusions obtained from thoracentesis of patients with histo-pathologically confirmed breast cancer. Prior to their use, all fluids were clarified by filtration and the following protease inhibitors were added: 0.1M 6-aminohexanoic acid, 10 mM aprotinin and 1.0 mM phenylmethyl sulfonylfluoride (final concentrations).

Malignant effusions, adjusted to pH 7.0 were loaded onto a series of three columns: Sepharose 4B, nonimmune murine immunoglobulin- and McAb F36/22-Sepharose 4B [Pak et al., Molec. Immun. 20:1369–1377 (1983)]. All columns were pre-equilibrated with PBS containing the protease inhibitors described supra. After loading, the antibody adsorbent was washed with 25–50 bed volumes of pH 7.0 phosphate buffer containing 1M NaCl. Subsequently, antigen was eluted using 0.2M citrate, pH 2.5, and 1 ml fractions were collected in tubes containing 1 ml of 1M Tris buffer, pH 8.4. Eluted material was dialyzed at 4° C. against deionized water and lyophilized to dryness.

Material obtained from the antibody adsorbent was dissolved in lectin affinity buffer (phosphate buffer, pH 7.0 containing 0.3M NaCl) and applied to a column packed with 10 ml of wheat germ lectin-Sepharose (Pharmacia).

After washing the column with 25 bed volumes of running buffer, bound components were eluted in the presence of N-acetyl-β-D-glucosamine (100 mg/ml). This material was extensively dialyzed against deionized water at 4° C. and lyophilized. The yield of isolated antigen was determined using an analytical balance and ranged from between 50 to 100 ng/ml of original effusion.

6.9.2. SIZE FRACTIONATION OF ANTIGEN

Malignant effusions obtained from patients with breast cancer (BCA) or ovarian cancer (OCA) or purified antigen preparation were size fractionated on columns packed either with Sephacryl S-400 or Sepharose CL-4B (Pharmacia).

A 0.5 ml sample was applied to a 1.5×100 cm chromatographic column packed with Sepharose CL-4B media. Fractions (2 ml) were eluted with phosphate buffer, pH 7.0, containing 1.0M NaCl and monitored for protein (absorbance at 280 nm) and antigen content (absorbance at 488 nm) using the enzyme immunoassay procedure described below.

Elevated levels of this ductal carcinoma antigen have also been detected in a high percentage of malignant effusions and in the sera of selected patients with ductal carcinomas (See Sec. 6.8.). As shown in FIG. 2, antigen occurring in effusions from both breast and ovarian cancer was found in high molecular weight fractions obtained after molecular sieve chromatographies. In all fluids studied, peak antigen activity eluted ahead of a 669,000 molecular weight marker protein.

6.9.3. POLYACRYLAMIDE GEL ELECTROPHORESIS

After purification of antigen from effusions, ductal carcinoma antigen was analyzed by sodium dodecyl sulfate-polyacrylamide gel electrophoresis (SDS-PAGE).

Samples (10 µg) were applied to 7.5% and 4% SDS-PAGE gels according to the method of Laemmli (1970, Nature, Lond. 227:680–685). Isolated material did not enter 7.5% SDS-PAGE gels but was visualized as an electrophoretically homogeneous component on 4.0% gels. This component did not stain with Coomassie blue R-250 protein stain, but did react when stained by the periodic-acid Schiff precedure to produce an intense band, indicating a high percentage of carbohydrate. [Fairbanks, Biochemistry 10:2606–2617 (1971)]. No structural differences were noted under non-reducing conditions.

The antigen was also analyzed by Western transfer of purified antigen onto nitrocellulose paper. Briefly, proteins were separated by SDS-PAGE and electrophoretically-transferred to nitrocellulose using the procedure of Towbin et al. [Proc. Natl. Acad. Sci U.S.A. 76:4350–4355 (1979)]. Residual protein-binding sites on the paper were blocked by incubation with 5% (w/v) bovine serum albumin in PBS, for 1 hour at 37° C. The nitrocellulose was then incubated with McAb F36/22 (10 µg/ml) or nonimmune murine serum for 18 hours at 4° C. After three washes (10 minutes each) with PBS, the paper was incubated for 1.0 hour at 37° C. with rabbit antiserum to murine immunoglobulin (Miles) diluted 500-fold in PBS. Following a wash procedure, as earlier, the nitrocellulose transfers were allowed to react with protein A-peroxidase conjugates (Zymed Laboratories) (500-fold diluted) for 0.5 hours at 37° C. The washed transfers were developed in substrate solution containing 0.1 mg 4-chloro-1-naphthol/ml of PBS with 0.003% hydrogen peroxide. After development (10–30 minutes at room temperature) the transfers were washed with water, air-dried and photographed. The results of Western transfers indicated that the purified material possessed multiple antibody-binding sites.

6.9.4. ENZYME IMMUNOASSAY

Immunoaffinity-purified ductal carcinoma antigen was quantitated using a sandwich-type of immunoassay procedure in which antigen bound onto a solid-phase antibody was detected using an enzyme-labeled secondary layer of antibody essentially described in Sec. 6.8.1.

Solid-phase antibody was prepared by incubating McAb F36/22 in plastic micro-wells |Nunc I Immunoplates (GIBCO, Grand Island, N.Y.)] overnight at 4° C. McAb (10 μg/ml) was dissolved in 50 mM carbonate-bicarbonate buffer, pH 9.6, prior to the coating procedure. After blocking non-specific protein binding sites on the plastic using a standard assay buffer [PBS pH 7.0 containing 1% (v/v) nonimmune murine serum and 1% (w/v) bovine serum albumin, or using borate ions), the plates were washed twice with assay buffer and used for the assay procedure.

Antigen-containing samples (sera, malignant effusions or chromatography fractions) were diluted in assay buffer and allowed to incubate with solid phase antibody for 1.5 hours at 37° C. Following a wash procedure, McAb F36/22 conjugated to horseradish peroxidase (Sigma, Type VI) was applied to each well (final concentration 0.5 μg/ml) and incubated for a further 1.5 hours at 37° C. After several washes, enzyme substrate was added to each well for 0.5 hours at room temperature. Substrate contained 0.4 mg o-phenylenediamine/ml of pH 5.0 citrate buffer containing 0.003% hydrogen peroxide. The enzyme reaction was stopped upon addition of 50 μg of 2N sulfuric acid, at which time optical absorbance (488 nm) was measured using a plate reader (Fisher Scientific Co. Pittsburgh, Pa.).

Specificity of immunoassay was examined by substituting the following antibody reagents as solid phase for McAb F36/22: McAb M7/105, distinct tumor antigen specific [Papsidero et al., Cancer Res. 43:1741–1747 (1983)]; McAb F5, prostate antigen specific [Papsidero, Hybridoma 2:139–147 (1983)]; and nonimmune murine serum. No dose response was observed when using these antibodies or when purified carcinoembryonic antigen (8 μg/ml) was used as antigen.

The high molecular weight component identified supra was effective in producing a dose response curve when using the enzyme immunoassay procedure as described below and in FIG. 3. Interestingly, borate ions acted to depress antigen activity, suggesting that carbohydrate may be present in or near the antibody-combining sites since borate forms complexes with cis-glycol groups of carbohydrates. While the PAS staining procedure indicated the presence of periodate-susceptible carbohydrates in the antigen, controlled periodate oxidation did not diminish antigen activity. Since cis-glycols are also the primary point of attack by periodate, terminal sugars of oligosaccharides may not be involved in the antigenic sites. Considering this latter observation, borate most likely interferes with the steric or ionic hindrance of the antibody approach to the epitope.

The format of this assay depends upon the occurrence of multiple antibody-combining sites on ductal carcinoma antigen, thus permitting a sandwich-type of procedure. Generally, monoclonal antibodies react with singly expressed determinants and therefore this procedure cannot be used for detection of any antigen.

6.9.5. PHYSICAL CHARACTERISTICS OF PURIFIED ANTIGEN

Physical characteristics of purified antigen included a single, major isoionic point near pH 4.2, a symmetrical high molecular weight peak upon molecular sieve chromatography and a broad pattern of migration upon two-dimensional immunoelectrophoresis.

Isoelectric focusing was done as described by Maidment et al. [J. Immun. Meth. 35:297–306 (1980)] using either pH 3–10 or pH 3–5 ampholines. After isoelectric focusing of antigen (5 μg) polyacrylamide gels were sectioned into 3 mm segments and individually placed in stoppered tubes containing 1 ml of degassed water. After 24 hours at 4° C., the contents of each vial were monitored for pH and antigen content using the enzyme immunoassay described supra (absorbance at 488 nm). Broad-range gels demonstrated the occurrence of a single major peak of immunoreactivity. Narrow-range gels (pH 3–5) indicated a similar isoionic point at pH 4.2.

Two-dimensional immunoelectrophoresis of immunoaffinity-purified ductal carcinoma antigen was performed as described by Weeke (1973. In A Manual of Quantitative Immunoelectrophoresis. Methods and Applications (eds. Axelson, N. H., Kroll J. and Weeke B., pp. 47–59, Universitetsforlaget, Oslo). Ten microgram amounts of antigen were subjected to electrophoresis with second-dimension agarose gels containing McAB F36/22 as ascites or nonimmune murine serum at a final concentration of 50 μg/ml. Immunoprecipitation reactions were visualized on dried gels using Coomassie blue R-250 protein stain. The broad pattern of migration observed upon two-dimensional immunoelectrophoresis confirmed the existence of multiple antibody-combining sites, as suggested from results using the sandwich type radioimmunoassay procedure supra.

Purified antigen was also subjected to isopycnic ultracentrifugation. Preparations of purified antigen (1 μg) in PBS were brought to 1.45 g cesium chloride/ml in the presence or absence of 4M guanidine hydrochloride. Samples were then subjected to $1.5 \times 10^6$ g in a Beckman SW-27 rotor at 10° C. for 72 hours. Fractions of 0.4 ml each were collected and assessed both for antigen content by enzyme immunoassay (absorbance at 488 nm) and density using an analytical balance. Purified antigen showed a density of approximately 1.3 g/ml in the presence of 4M guanidine hydrochloride, and 1.45 g/ml in its absence. Density measurements were consistent with those commonly observed for mucins associated with cervix and colonic mucosa [Carlstedt et al., Biochem. J. 211:13–22 (1983); Hascall and Kimura, Meth. Enzym. 82:769–800 (1982)].

6.9.6. LECTIN BINDING ABILITY OF PURIFIED ANTIGEN

Purified antigen (0.4 μg) was allowed to react with excess amounts (200 μl) of 50% (v/v) suspensions] of the following lectins at 4° C. for 18 hours: concanvalin A-, lentil lectin-, wheat germ- and peanut agglutinin-Sepharose (Sigma). Subsequently, serial dilutions of the supernatants were assayed for antigen content. Results were expressed as percentage bound as compared to control non-derivatized Sepharose. Although rich in carbohydrate, as demonstrated by reactivity with Schiff reagent, purified antigen showed a preferential reactivity with wheat germ lectin (Table VI). A low or negligible interaction was noted to occur with concanavalin A, peanut agglutinin and lentil lectin. Therefore, carbohydrate groups available for such interaction were not highly heterogeneous in composition. Since mucin-like glycoproteins commonly possess a limited number of oligosaccharide units which are highly repetitive, these results were not unexpected [Hascall and Kimura, Meth. Enzym. 82:769–800, (1982)].

TABLE VI

REACTIVITY OF IMMUNOAFFINITY-PURIFIED DUCTAL CARCINOMA ANTIGEN WITH LECTINS[a]

| Solid phase | % bound |
| --- | --- |
| Control[b] | 0 |
| Concanavalin A | 19 ± 14 |
| Wheat germ lectin | 95 ± 6 |
| Lentil lectin | 12 ± 4 |
| Peanut agglutinin | 8 ± 7 |

TABLE VI-continued

REACTIVITY OF IMMUNOAFFINITY-PURIFIED DUCTAL
CARCINOMA ANTIGEN WITH LECTINS[a]

| Solid phase | % bound |
|---|---|

[a]Four preparations of antigen were tested and results indicate the mean value ± SEM. McAb F36/22 derivatized to Sepharose served as a positive control (60 ± 15% bound). No significant binding was observed with the following antibody adsorbents: McAb M7/105 [distinct tumor antigen, Papsidero et al., Cancer Res.)], McAb F5 [prostate antigen specific, Papsidero et al., Hybridoma)] and polyclonal rabbit antiserum to whole human serum.
[b]Negative control, non-derivatized Sepharose.

6.9.7. EFFECTS OF PHYSICAL TREATMENT, CHEMICAL MODIFICATIONS AND ENZYMES ON THE BINDING OF McAb F36/22 TO PURIFIED ANTIGEN

Purified antigen (1 μg) was subjected to heat treatment (60° C. for 5 hours) in the presence or absence of 0.1N NaOH or 0.1N HCl. Treatments using periodic acid were performed as follows: immunoaffinity-purified antigen was dissolved in periodic acid (50 mM in 0.2M acetate, pH 4.0). The mixture was incubated for 24 hours at 4° C., at which time residual periodate was removed by addition of 50 μl glycerol [10% (v/v)] for 4 hours at 4° C. Each treatment was terminated by addition of cold enzyme assay standard buffer (PBS containing murine serum and albumin) and residual antigen content was determined as described supra using the enzyme immunoassay (absorbance at 488 nm).

As shown in FIG. 4, the activity of purified antigen was not affected upon exposure to acid or after heating. In contrast, no antigen activity was detectable following treatment with base.

The effects of proteolytic enzymes and glycosidase were also determined. Proteolytic enzymes were tested by incubating purified antigen with enzyme (mass ratio of 100:1- antigen:enzyme) in a final volume of 0.1 ml for 18 hours at 37° C. Reactions were stopped by addition of protein buffer prior to enzyme immunoassay to determine residual antigen content. Control tubes contained identical amounts of antigen in protein buffer in which instance the proteolytic enzyme to be studied was added immediately before the immunoassay procedure. The following enzymes, and appropriate buffer systems utilized, where tested: pepsin (Boehringer-Mannheim) (PBS); trypsin (Sigma) (PBS); papain (Worthington) (Tris, pH 7.2/10 mM cysteine/1 nM EDTA); and pronase (Boehringer-Mannheim) (PBS).

Treatments using glycosidase enzymes were performed similarly, except that incubation with antigen (final concentration 25 ng/ml) was allowed to proceed for 72 hours at 37° C. The following enzymes were used, along with the respective buffer system employed: 0.02 mU/ml neuraminidase (Boehringer-Mannheim) (acetate buffer, pH 5.0, containing 1 mM $MgCl_2$); 740 mU/ml β-galactosidase (Sigma) (PBS containing 1 mM $MgCl_2$); and 2 mU/ml α-mannosidase (Sigma) (PBS) [final concentrations].

Each of these treatments failed to decrease activity of the purified antigen. These data suggest that antibody combining sites are either not specifically hydrolyzed by these reagents or may reside at site impervious to enzyme degradation, possibly due to a high carbohydrate content.

6.10. IN VITRO IMMUNOHISTOLOGICAL APPLICATIONS OF MONOCLONAL ANTIBODY F36/22

6.10.1. IMMUNOPEROXIDASE STAINING OF TUMOR SPECIMENS BY McAb F36/22

In a first set of experiments, sections of formalin-fixed and paraffin-embedded human tumor tissues were used for immunoperoxidase staining as described previously [Heyderman, E. and Neville, A. M., J. Clin. Path., 30:138–140(1976)]. Briefly, hydrated sections were treated with 20% pre-immune rabbit serum and then incubated with 100 μl F36/22 hybridoma culture fluid (7.5 μg antibody/ml) for 1 hour at room temperature. Following 2 washes in D-PBS, peroxidase-conjugated rabbit antibodies against murine immunoglobulin (1/30 dilution; Accurate Chemical Corp.) were applied for 1 hour and the slides further washed. Antibody-enzyme conjugates were pre-adsorbed with solid-phase human immunoglobulin to avoid spurious binding due to the possible presence of human globulin in tumor specimens. Enzyme activity was revealed using a diaminobenzidine/$H_2O_2$ substrate [Heyderman and Neville, (1976), supra]. For some experiments, unfixed cryostat sections of fresh breast tumors were used to assess antibody reactivity.

Overall, 17 out of 22 specimens of intraductal breast carcinoma showed the presence of antigen recognized by McAb F36/22 (TABLE VII). Several specimens of non-mammary tumors also shows immunoperoxidase staining. However, as summarized in TABLE VII, these specimens produced a weak staining intensity and/or low frequency of positive reactions. This cross-reactivity was restricted to adenocarcinomas; other tumor types (sarcoma, lymphoma, myeloma) were consistently negative. Benign lesions of the breast were further tested with the immunoperoxidase technique using F36/22; these included 3 fibroadenomas and 6 fibrocystic disease. Two specimens each showed positive staining reaction at the apical membrane portion of ductal elements. Sections obtained from normal pancreas (n=4), prostate (n=5), colon (n=3), liver (n=4), spleen (n=2) and skin (n=3) were negative, as was a specimen of DMBA-induced mammary cancer of the rat.

TABLE VII

IMMUNOPEROXIDASE STAINING OF TUMOR SPECIMENS USING MONOCLONAL ANTIBODY F36/22[a]

| | Number of Specimens | | |
|---|---|---|---|
| Tumor Type | Tested | Strongly Positive[b] | Weakly Positive[c] | Negative |
| Breast Carcinoma | 22 | 10 | 7 | 5 |
| Colon Carcinoma | 10 | 1 | 2 | 7 |
| Lung Carcinoma | 3 | 0 | 1 | 2 |
| Uterus Carcinoma | 10 | 1 | 3 | 6 |
| Liver Carcinoma | 2 | 0 | 0 | 2 |
| Thyroid Carcinoma | 1 | 0 | 0 | 1 |
| Bladder Carcinoma | 6 | 0 | 0 | 6 |
| Prostate Carcinoma | 5 | 0 | 1 | 4 |
| Pancreas Carcinoma | 2 | 0 | 0 | 2 |
| Lymphosarcoma | 3 | 0 | 0 | 3 |
| Lymphoma | 2 | 0 | 0 | 2 |
| Plasmacytoma | 1 | 0 | 0 | 1 |
| Melanoma | 2 | 0 | 0 | 2 |
| Astrocytoma | 2 | 0 | 0 | 2 |

[a]All specimens examined represent formalin-fixed and paraffin-embedded tissues examined using monoclonal antibody F36/22 at a concentration of 7.5 μg/ml.
[b]Greater than 10% of the tumor cells exhibiting intense cytoplasmic staining.
[c]Less than 10% of the tumor cells exhibiting staining or exhibiting a weak staining reaction limited to the luminal surface of ductal elements.

In an expanded investigation of the in vivo tissue distribution of the epitope recognized by McAb F36/22, immunoperoxidase staining was performed on extra-mammary tumor specimens using a variation of the technique described supra.

Paraffin-embedded blocks of tissue were obtained from the Pathology Departments of St. Joseph's Intercommunity Hospital and Roswell Park Memorial Institute, Buffalo, N.Y.

All tissues were fixed immediately in 10% buffered formalin, embedded in paraffin, and sectioned at 3 to 4 μm for these studies. The sections were collected on slides pretreated with ovalbumin and glycerine and heated at 70° C. for 5 minutes to increase the adherence of the sections to the glass slides.

Hydrated sections were treated with 10% preimmune rabbit serum in 1% ovalbumin and then incubated with 100 μl of hybridoma culture fluid (10 μg antibody/ml) for 90 minutes at room temperature. Following washes in D-PBS containing 0.01% Nonidet P-40, peroxidase-conjugated rabbit antibodies against murine immunoglobulin (1/30 dilution; Accurate Chemical Corp.) were applied 45 minutes. Human immunoglobulin, convalently-linked to Sepharose beads was used to pre-adsorb the antibody-enzyme conjugate in order to prevent binding to human immunoglobulin that might be present in the tumor specimens. In most cases, enzyme activity was revealed using diamino-benzidine/$H_2O_2$ substrate in phosphate buffer, pH 6.3. In very sanguinous tissues which have large amounts of endogenous peroxidases, amino-ethyl-carbazole (4 mg/ml; Sigma)/$H_2O_2$ was used as the substrate to better ascertain specific binding. In addition to the normal control substitution experiments, which included PBS in place of the primary antibody, peroxidase-conjugated antibody alone and culture fluid from a myeloma cell line (FLOPC-21), which secreted an irrelevant IgG3 antibody, were used. The intensity of the immunoreaction product was scored using a 0 to +++ scale for TABLE VIII, however, in order to facilitate statistical evaluations of the staining intensity data, corresponding numerical values of 0 to 3 were utilized.

The results of immunoperoxidase staining on a large group of extramammary tumors are shown in TABLE VIII. A varying incidence of antigen expression was observed for these specimens. The majority (54/58) of immuno-positive tumors were histologically classified as adenocarcinomas and no detectable antigen was expressed by other carcinoma types, including basal cell carcinoma, bronchogenic carcinoma (squamous, large cell and oat cell), squamous cell carcinomas of the rectum and endocervix, malignant melanocarcinoma, esophageal carcinoma (squamous and adenocarcinoma) and squamous cell carcinoma of the bladder. The other 4 positive tumors were transitional cell tumors of the bladder and renal pelvis. The predominant location of staining in the majority of these positive tumors was the apical luminal surface of the epithelial cells, although the intensity of staining was usually lower than that observed for breast carcinomas (TABLE VIII).

For several carcinoma sites, including colon, pancreas, jejunum, stomach, prostate and ovary, the adjacent tissue was consistently negative for expression of antigenic determinant, but the tumor was positive. Of additional interest, a few specimens of pancreas and colon carcinomas showed expression of the antigenic determinant in the epithelial elements of the adenocarcinoma and also in apparently normal tissue directly adjacent to the carcinoma, whereas normal tissue further distal to the tumor was negative. No detectable reactivity with a large panel of tumors of mesenchymal origin was observed (TABLE VIII), including lymphosarcomas, myelomas, astrocytomas, leukemias and sarcomas.

TABLE VIII

IMMUNOPEROXIDASE STAINING OF
EXTRA-MAMMARY TUMORS WITH McAb F36/22

| Tissue Examined | No. Staining/ No. Examined | Predominant Location of Stain[a] | Intensity of Stain[b] | x̄ % Positive cells (range)[c] |
|---|---|---|---|---|
| Gastric Carcinoma | 5/10 | S | + to ++ | 40 (10–60) |
| Jejunal Carcinoma | 1/2 | S | + | 30 |
| Colonic Carcinoma | 3/9 | S | + to ++ | 60 (50–80) |
| Cholangic Carcinoma | 6/7 | S | + to ++ | 60 (30–90) |
| Pancreatic Carcinoma | 4/10 | S | + | 40 (10–90) |
| Thyroid Carcinoma | 1/2 | S | + | 40 |
| Endocervical Carcinoma | 1/2 | S | + to ++ | 80 |
| Endometrial Carcinoma | 9/13 | S/C | + to +++ | 70 (30–90) |
| Fallopian Tube Carcinoma | 0/2 | | | |
| Ovarian Carcinoma | 15/15 | S | + to +++ | 80 (70–90) |
| Prostatic Carcinoma | 2/8 | S | + | 10 (20–20) |
| Renal Carcinoma | 3/6 | S | + to +++ | 40 (20–60) |
| Bronchogenic Carcinoma | 5/13 | S/C | + to +++ | 70 (50–90) |
| Ovarian Cystadenoma | 3/3 | S/C | + to +++ | 40 (20–80) |
| Bladder Carcinoma | 2/5 | C | ++ | 30 (20–40) |

[a]S = Marginal and/or luminal surface; C = cytoplasmic; S/C = surface and/or cytoplasmic.
[b]Intensity scale: – negligible; + weak; ++ moderate; +++ strong.
[c]Percent of positive staining cells was estimated by observing the number of positive cells in replicate 100× fields.
[d]No staining was observed in the following extra-mammary tumor specimens (the number in parenthesis indicates the number of samples examined): esophageal carcinoma (5); hepatic carcinoma (2); parotid gland carcinoma (3); submaxillary gland. carcinoma (1); seminoma (2); malignant melanoma (3); basal cell carcinoma (4); squamous cell carcinoma (3); sebaceous gland carcinoma (1); leukemias (4); multiple myeloma (3); meningioma (2); astrocytoma (3); lymphosarcoma (6); Kaposi's sarcoma (1); fibrosarcoma (3); glomus tumor (1); carcinoid (2); teratoma (4); hidroadenoma (4); myoxma (3); neuroma (3); hemangioma (2); hamartoma (2); lymphangioma (1); lipoma (4); trichoepithelioma (3); fibroxanthoma (2); nevus (benign) (1);

6.10.2. IMMUNOREACTIVITY OF McAB F36/22 WITH NORMAL MAMMARY TISSUE, MEMBRANE PREPARATIONS AND MILK

McAb F36/22 was tested for its ability to react with mammary membranes using adsorption analysis and direct binding radioimmunassay procedures. To obtain tissue membranes, normal breast tissue was homogenized in D-PBS containing protease inhibitors (0.5 mM PMSF and 1.0 mM epsilon-aminocaproic acid). All steps were performed at 4° C. Cell debris and nuclei were pelleted at 2,000×g and the supernatant was further centrifuged at 40,000×g to obtain a crude membrane fraction. The membranes were washed three times with D-PBS and adjusted to 2 mg protein/ml.

Membranes from human milk were isolated as follows: the cream fraction was washed 5 times with D-PBS to remove whey proteins and was quickly frozen. The cream was then slowly thawed, thereby increasing the rupture of membrane globules, and then was shaken vigorously in D-PBS containing 1 mM $MgCl_2$. When butter formation was observed, the suspension was centrifuged at 100,000×g for 1 hour. Membranes were resuspended in D-PBS at 2 mg protein/ml.

For direct binding measurements, 50 µl samples of membrane preparations were added to wells of glutaraldehyde-sensitized microtiter plates. After adhering overnight, the wells were washed twice with 0.25% glycine and then 4 times with D-PBS containing 1% bovine serum albumin. The assay was performed in triplicate using 100 µl samples of McAb F36/22 which were incubated with the membranes for 90 minutes at room temperature. The remainder of the assay was performed as in Section 6.5., for CS-RIA procedure.

Membrane fractions obtained by the foregoing procedures from both tissues and human milk fat globules were examined along with the frozen sections of normal mammary tissues. As shown in TABLE IX, antibody F36/22 directly bound to all membrane preparations examined, and was able to be adsorbed by these specimens. Immunoperoxidase data confirmed the identity of the reactive antigen as a component of the ductal epithelial surface membrane.

TABLE IX

IMMUNOREACTIVITY OF NORMAL MAMMARY TISSUES AND MEMBRANE PREPARATIONS

| Specimen | Reactivity with Antibody F36/22 |
| --- | --- |
| Mammary Tissues[a] | + |
| Membranes[b] | |
| Tissues | + |
| Milk Fat Globule | + |

[a]Cryostat sections of frozen mammary tissues (n = 3) were examined by standard immunoperoxidase staining techniques (see Section 6.10.1).
[b]Membrane preparation at 2 mg protein/ml were tested for their immunoreactivity using absorption analysis and direct-binding radioimmunoassay (see Section 6., and 6.5., respectively).

A second set of experiments testing the reactivity of McAb F36/22 with normal tissues was performed using the immunoperoxidase staining technique. The results are summarized in TABLE X.

In general, positive staining was restricted to the epithelial elements of a few exocrine glands and their associated ducts. These included sweat glands, sebaceous glands, and endometrial glands. Other tissues with positive staining were respiratory alveoli, ductuli efferentes of epididymis, fallopian tube and the distal tubules and collecting ducts of the kidney. These tissues exhibited a very weak apical luminal staining.

There was no relationship between the degree of positive staining in endometrial glands and the different phases of the menstrual cycle. Additionally, the tissue components of ovary, colon, stomach, pancreas, prostate, and gall bladder did not contain detectable levels of the antigen determinant recognized by McAb F36/22, whereas the adenocarcinomas of these histotypes did express detectable levels to a varying incidence. The bile ducts of liver, the acinar cells of the pancreas, and the serous demilunes of the salivary gland were all negative for the expression of the epitope.

TABLE X

IMMUNOPEROXIDASE STAINING OF NORMAL TISSUE WITH McAb $F_{36}/_{22}$[a]

[a]. Normal tissues distal to tumors examined in the present study were also evaluated for expression of this antigen determinant, but these data were not included in the above numbers.

Positive Staining Restricted to Epithelial Elements of

The globules and cell surfaces of sebaceous glands (5/5)[b], alveolar epithelium of lung (4/5), sweat glands and associated ducts (5/5), ductuli efferentes of epididymis (3/3), endometrial glands and ducts (8/8), fallopian tube (4/5), distal tubules and collecting ducts of kidney (4/4).

[b]. No. of tissues staining/No. of tissues examined.

No Staining of Tissue Elements of

Esophagus (2)[c], stomach (3), small intestine (3), appendix (3), colon (5), pancreas (4), gall bladder (2), liver (5), parotid gland (2) submaxillary gland (3), thyroid (3), adrenals (2), spleen (3), tonsil (2), lymph node (2) bone marrow (3), prostate (5), ovary (15), testes (4), nervous tissue (5), skin (5), myocardium (3), trachea (1) and bladder (2).

[c]. The No. in parentheses represents total No. examined.

6.10.3 IMMUNOPEROXIDASE STAINING OF HUMAN BREAST TISSUES AND TUMORS

Non-malignant and primary breast tumor specimens were obtained at surgery. Freshly obtained autopsy specimens of normal tissues and distant metastatic lesions were also examined. All tissues were fixed immediately in 10% buffered formalin, embedded in paraffin, and sectioned at 3 to 4 µm for these studies. The sections were collected on slides pretreated with ovalbumin and glycerine and heated at 70° C. for these studies. The sections were collected on slided pretreated with ovalbumin and glycerine and heated at 70° C. for 5 minutes to increase adherence of the sections to the glass slides. The immunoperoxidase staining technique described for the expanded investigation in Section 6.10.1. was employed.

The results of tissue staining for normal resting breast, benign and malignant breast tumors are presented in TABLE XI. In general, the normal resting breast parenchyma exhibited delicate, but weak, immunoperoxidase staining restricted to the apical luminal surface of epithelial cells. Benign tumors of the breast displayed similar location of the staining reaction, except that the intensity of the reaction was generally greater. All gynecomastia specimens examined showed positive immuno-reactivity consistent with that observed in the benign conditions. Primary breast tumors, however, displayed significant variations in the percentage of cells stained in any given tumor, in the intensity of the staining reaction and, and in the location of the immunoreaction. As is summarized in TABLE XI, expression or lack of expression of the antigenic determinant did not correlate with the grade of the tumor. However, McAb F36/22 predominantly stained the surface membranes of luminal epithelial cells in well-differentiated carcinomas and those cancer cells bordering lumina within the in situ and comedo tumors. Poorly-differentiated tumors, when stainable, most often exhibited focal cytoplasmic staining. Intensity of the reaction product varied from specimen to specimen (TABLE XI).

Furthermore, antibody at 200 ng/ml was capable of staining greater than 95% of the original immunopositive cells. Thus, the present experiments were performed at antibody excess. Increasing the incubation times also did not affect the sensitivity of the assay.

TABLE XI

INDIRECT IMMUMOPEROXIDASE STAINING OF HUMAN BREAST TISSUE WITH McAb F36/22

| Tissue Examined | No. Staining/ No. Examined | Predominant Location of Stain[a] | Intensity of Stain[b] | $\bar{x}$ % Positive cells (range)[c] |
|---|---|---|---|---|
| Normal | | | | |
| Resting Breast | 4/4 | S | + | 70 (40–90) |
| Non Malignant Lesions | | | | |
| Fibrocystic disease | 6/6 | S | + to +++ | 70 (40–90) |
| Fibroadenoma | 6/6 | S | + to +++ | 80 (70–90) |
| Cystosarcoma Phylloides | 1/1 | S | +++ | 90 |
| Papilloma | 2/2 | S | + to ++ | 90 (80–100) |
| Gynecomastia | 5/5 | S | + to +++ | 70 (20–90) |
| Malignant Lesions | | | | |
| Ductal Carcinoma: | | | | |
| Tubular type | 0/2 | | | |
| Moderately diff. | 4/4 | S/C | + to +++ | 30 (20/50) |
| Poorly diff. | 10/13 | | + to +++ | 70 (30–90) |
| Comedo type | 5/5 | S/C | + to +++ | 80 (50–90) |
| Infiltrating Ductal Carcinoma: | | | | |
| Well diff. | 3/4 | S | + to +++ | 50 (40–80) |
| Well–Mod. diff. | 1/1 | S/C | +++ | 90 |
| Moderately diff. | 7/10 | S/C | + to +++ | 60 (10–90) |
| Mod.–Poorly diff. | 8/9 | S/C | +++ | 90 (80–100) |
| Poorly diff. | 17/18 | C | + to +++ | 60 (40–90) |
| Mucoid Carcinoma | 3/3 | S/C | ++ to +++ | 90 (80–100) |
| Lobular Carcinoma | 8/9 | C | + to +++ | 80 (50–90) |
| Medullary Carcinoma | 1/1 | C | ++ to +++ | 60 |
| Squamous Cell Carcinoma | 1/1 | C | + to ++ | 50 |
| Lymphosarcoma | 0/1 | | | |
| Metastatic Lymph nodes | 5/12 | S/C | + to +++ | 50 (30–90) |

[a]S = marginal and/or luminal surface; C = cytoplaasmic; S/C = surface and/or cytoplasmic.
[b]Intensity scale: − negative; + weak; ++ moderate; +++ strong.
[c]Percent of positive staining wells was estimated by observing replicate 100× fields of view.

6.10.4. EFFECT OF VARYING McAb F36/22 CONCENTRATION AND INCUBATION TIMES ON IMMUNOPEROXIDASE STAINING RESULTS

To determine if the lack of detectable antigen expression in some tumors was merely reflecting an inadequate antibody concentration, the following study was performed. Two reference breast carcinomas which were known to be positive for the expression of the epitope recognized by McAb F36/22 were serially sectioned. Serial dilutions of McAb F36/22 (initial concentration: 10 µg/ml) were incubated with the sections which then were evaluated by immunoperoxidase staining. The highest dilution which exhibited immunopositivity when compared to the initial concentration was determined.

Increasing the concentration of McAb F36/22 from 10 to 20 µg/ml did not significantly increase the percentage of tumors exhibiting positive immunoperoxidase staining.

6.10.5. ESTROGEN RECEPTOR LEVELS AND IMMUNOPEROXIDASE STAINING

To determine if the staining patterns recognized by McAb F36/22 were related to estrogen receptor status, 60 breast tumors of known estrogen receptor levels were stained by immunoperoxidase techniques as previously outlined. The estrogen receptor levels of these specimens were determined at the Buffalo General Hospital, Department of Clinical Chemistry, as described by Rosen, P. P. et al. [Cancer Res. 35:3187–3194(1975)].

Breast cancer specimens of known estrogen receptor level (n=60) 42 ER-rich, 18 ER-poor, were examined by immunoperoxidase techniques. The percentage of positive cells, the mean+S.D., (69±30) in the ER-rich carcinomas was greater (p less than 0.001) than that exhibited in ER-poor cancers (33±37). In addition, the intensity of the staining reaction associated with ER-rich cancers (2.1±0.8) was significantly greater (p less than 0.001) than the reaction product observed in ER-poor carcinomas (1.0±0.9), as assessed using the semi-quantitative technique of immunoperoxidase staining.

6.11. IN VIVO APPLICATIONS OF MONOCLONAL ANTIBODY F36/22

6.11.1. EXPERIMENTAL INDUCTION OF SOLID TUMORS IN MICE

Human tumor cells were mechanically-harvested from tissue culture flasks and washed with serum-free RPMI-1640 medium. Cell preparations showing greater than 90% viability, as assessed with trypan blue, were used to produce solid tumors in mice. Athymic female Swiss nude (nu/nu) mice were given subcutaneous injections of 0.2 ml containing 4-10×10$^6$ viable tumor cells. MCF-7 and BT-20 (human breast carcinoma), Chago (human lung carcinoma) and Daudi (lymphoblastoid cells) were used. Tumor dimensions were subsequently monitored at daily intervals using calipers and the tumor volume was calculated using a formula described by Kovnat, A. et al. [Cancer Res., 42:3969-73 (1982)].

6.11.2. McAb F36/22 TARGETING: IN VIVO TUMOR LOCALIZATION

To evaluate whether immunotherapeutic effects could be attributed to a direct interaction between tumor and antibody, targeting experiments were performed to determine the tissue distribution of injected radio-antibody.

For one set of antibody targeting experiments, purified immunoglobulins were labelled with iodine-125 to a specific activity of 5 Ci/mM] [Fraker, P. J. and Speck, Jr., J. C., Biochem. Biophys. Res. Commun., 80:849–57(1978)]. Athymic mice bearing human tumor xenografts induced by MCF-7 or Chago cells, were given a single intraperitoneal injection of radiolabelled immunoglobulin (10–20 µCi) on day 0. On day 7, the animals were exsanguinated by cardiac puncture and tumors and organs were removed. After weighing each tissue, radioactivity was measured in a well-type gamma counter. The results were expressed as a localization ratio, i.e., cpm per gram of tissue (tumor or organ) divided by cpm per gram of blood.

As shown in TABLE XII, McAb F36/22 localized to breast tumors in greater amounts per gram of tissue than other organs examined. Effective targeting of radio-antibody to breast tumor xenografts indicates a direct interaction between tumor cells and F36/22 monoclonal antibody. This targeting effect was observed with the use of control immunoglobulin preparations or against lung carcinoma xenografts (TABLE XII).

TABLE XII

TARGETING OF RADIOLABELLED MONOCLONAL ANTIBODY (F36/22) IN ATHYMIC MICE BEARING HUMAN TUMOR XENOGRAFTS[a]

| Tissue[b] | Localization Ratio[c] |
|---|---|
| Blood | 1 |
| Breast Carcinoma (MCF-7) | 3.4 ± 0.5 |
| Lung Carcinoma (Chago) | 0.7 ± 0.1 |
| Lung | 1.2 ± 0.3 |
| Liver | 0.5 ± 0.2 |
| Spleen | 0.4 ± 0.1 |
| Kidney | 0.5 ± 0.2 |
| Brain | 0.5 ± 0.1 |

TABLE XII-continued

TARGETING OF RADIOLABELLED MONOCLONAL ANTIBODY (F36/22) IN ATHYMIC MICE BEARING HUMAN TUMOR XENOGRAFTS[a]

| Tissue[b] | Localization Ratio[c] |
|---|---|

[a]Athymic mice (4 per group) were each implanted with 2 human tumor xenografts on contralacteral sites of the back. These consisted of breach (MCF-7) and lung (Chago) carcinomas. Xenografts were of similar size at onset of the experiments (between 5 and 15 mm$^3$). Each animal received between 10 to 15 µCi of radiolabelled monoclonal antibody (F36/22) by the intraperitoneal route.
[b]Tissues and blood were harvested 7 days post injection.
[c]Localization Ratio: cpm per gram tissue (tumor or organ) divided by cpm per gram of blood, (mean ± S.D.).

In a second set of targeting experiments, BT-20 (human breast carcinoma), and Chago (human lung carcinoma) were used. The growth pattern of the xenografts was carefully monitored in order to consistently work with similar sizes of growing tumors. In vivo tumor localization was performed essentially the same as above. Twenty micrograms of $^{125}$I-labelled McAb F36/22 (specific activity, 1 µCi/µg) was injected intraperitoneally using four groups of nude mice (n=3) bearing either BT-20 or Chago tumors. One group of mice was sacrificed at sequential days after administration of radiolabelled McAb F36/22. Twelve tissues were removed (blood, liver, lung, spleen, heart, skeletal muscle, skin, kidney, intestine, brain, and tumor), and the tissue distribution of the labelled antibody was determined with a Gamma counter. Tissue levels were calculated in disintegrations per minute per gram of tissue. Blood levels were taken as the reference background so that relative antibody uptake into tissues (localization ratio) was determined to be the ratio of disintegrations per minute per gram of tissue divided by the disintegrations per minute per gram of blood. The uptake of McAb in the BT-20 tumors was 5.7 (±0.4), (mean±standard deviation) fold greater than the blood background (p less than 0.02), at 7 days post injection; whereas no other tissue including Chago tumors showed statistically significant activity above blood levels. In contrast, normal mouse $^{125}$I-labelled antibody (γ3 subclass) showed no specific uptake into any tissues or tumors sampled. Significant specific uptake of McAb F36/22 was also seen in MCF-7 breast carcinoma, which gave a localization ratio of 3.4 (±0.5), as compared to blood levels (p less than 0.05).

6.11.3. IN VIVO PASSIVE IMMUNOTHERAPY WITH McAb F36/22

For one set of therapy studies, mice with progressively growing human tumors (MCF-7, Chago or Daudi) were given a single intraperitoneal injection at day 0 of either monoclonal antibody F36/22 or control immunoglobulin. One hundred micrograms were administered in a total volume of 0.2 ml sterile PBS. Mean tumor volumes at day 0 were: MCF-7, 57 mm$^3$; Daudi, 59 mm$^3$; Chago, 105 mm$^3$. Post-therapy tumor volumes were taken at daily intervals and statistical evaluations were performed using Student's t-test. Based upon these measurements the tumors were scored as either progressive, static, or regressive. For each experiment mice were monitored for one week, at which time tumor specimens were excised for histological examination. Results obtained using caliper measurements indicated that breast carcinoma xenografts treated with antibody F36/22 had regressed to approximately 15% of their pre-treatment volumes (57 to 7 mm$^3$) at day 7. As expected with the use of a murine host, non-immune mouse IgG produced no such effect at the same dose level. The therapeutic effect of antibody F36/22 was evident by day 4 post-therapy, when a significant (p less than 0.01) decrease (approximately 75%) in breast tumor volumes was observed. Replicate groups of antibody-treated mice which were observed for 2 weeks demonstrated breast tumor xenografts exhibiting no detectable capacity for regrowth during this period. Histological examination of breast tumors obtained 7 days post-therapy indicated a significant amount of tumor cell necrosis accompanied by initial stages of fibrosis. In contrast, the histological picture of control tumors treated with non-immune IgG was consistent with the normal histology of MCF-7 breast carcinoma xenografts.

The therapeutic specifity of antibody F36/22 was evaluated against two non-mammary human tumor xenografts implanted in nude mice. For these experiments a slow growing lymphoma (Daudi) and rapidly multiplying lung carcinoma (Chago) were used. Results indicate that antibody treatment was ineffective in causing regression of these tumors within 4 days post-therapy. Further, at 7 days post-therapy, the lymphomas were at over 300% of their day 0 volume (from 59 to 222 mm$^3$ at days 0 and 7, respectively). A similar progression of lung carcinoma xenografts was also observed (105 and 706 mm$^3$ at days 0 and 7, respectively).

The effects of McAb against tumors in vivo were tested in another experiment. One group of mice (n=4), bearing human breast carcinoma (BT-20) were inoculated intraperitoneally with 100 µg of purified [Ey, P. L. et al. Immunochem., 15:429–436 (1978)] McAb F36/22. A significant reduction (40%) of tumor volumes was seen for each of the individual mice one day following injection of McAb F36/22 (p less than 0.001 for each tumor as compared to pre-treatment volumes). Tumor volumes were measured daily with precision caliper and calculated by the 3 diameter product. No tumor volume reduction occurred during the 7 days following administration of the control antibody.

In order to test reproducibility and statistical significance of the McAb therapy, further experiments were performed. After 3 weeks to 2 months post-implantation, 26 BT-20 breast tumors of sizes ranging from 12 to 199 mm$^3$ (mean, 61 mm$^3$) were produced. These tumor-bearing mice were injected with either 100 µg of purified McAb F36/22 or one of 2 identically-purified control antibodies (one a γ3 myeloma protein with no known specificity, the other a γ2a complement-fixing McAb with no cell binding specificity to BT-20 cells). Fourteen mice with tumors ranging from 18 to 199 mm$^3$ (mean±SD, 62±46 mm$^3$) were each injected intraperitoneally with 100 µg of McAb F36/22 in PBS, and 12 mice with tumors ranging from 12 to 149 mm$^3$ (mean±SD, 61±42 mm$^3$) with the same amount of control antibody (7 of the control mice with the γ3 protein and 5 of the control mice with the γ2a McAb). Therapy of breast cancer with McAb F36/22 resulted in a rapid reduction in tumor size. Tumor regression continued for about 3-4 days post-therapy and thereafter the tumors remained at approximately 25 percent of their pretreatment volume. In comparison, breast tumors were at 115 (±37) percent of original volume after treatment with control immunoglobulin. Measurements of the control antibody-treated group showed 6 mice had slowly enlarging tumors; 2 tumors were stable and 4 tumors were slowly regressing in volume over the 7 days of the experiment. Similar variations of growth patterns were typically seen in breast carcinoma xenografts as thoroughly described by others [Ozzelo, L. and Sordat, M., Eur. J. Cancer, 164:553–559 (1980)]. The McAb F36/22 produced no regression of Daudi lymphoid tumors or fast growing Chago lung carcinomas. The BT-20 tumors were significantly reduced in volume (p less than 0.001) as compared to controls at 24 hours post-therapy and remained at a decreased volume for the course of the 7 day experiment. The mice with closely matched tumor sizes were segregated into groups consisting of small and large BT-20 tumors, in order to judge the possible influence of pre-treatment tumor size on the amount of tumor volume reduction following therapy. The first group consisted of 11 mice with tumors ranging from 26–49 mm$^3$. The second group had 9 mice with tumor volumes ranging from 60–88 mm3. The smaller tumors decreased to 5(±3) mm$^3$, 4 days after McAb F36/22 treatment as compared to 51(±25) mm$^3$ for control antibody treated mice (p less than 0.001) (TABLE XIII). The larger tumors were reduced to 25(±18) mm$^3$ 4 days after McAb F36/22 therapy, as compared to 74(±20) mm$^3$ for controls (p less than 0.005) (TABLE XIII). No statistically significant difference was observed in the percentage of tumor volume reduction between the larger and smaller tumor groups.

Tumor histology which was taken before therapy and at 1, 3 and 5 day intervals after the injection with 100 µg of McAb F36/22, demonstrated extensive necrosis of tumor cells on days 1, 3 and 5. On day 1, tumor cell necrosis was most prominent in the central region of the tumor, leaving a semi-circular ring of intact tumor cells (1 to 20 cells thick) at the periphery of the tumor. Acute inflammatory cell infiltration was also seen. By day 3, tumor contraction was observed, accompanied by both chronic and acute inflammatory cells. On day 5 scar tissue activity was evident along with a predominantly chronic inflammatory pattern of cell infiltration. These histological changes appear to be very similar to those observed by others using a polyclonal sera on a virally infected chemically induced murine sarcoma [Ward, E. W. et al., J. Natl. Cancer Inst. 69:509–515 (1982)]. Extensive tumor cell necrosis was also seen for MCF-7 breast tumors treated with McAb F36/22 and no histological changes were seen in identically treated Chago tumors as compared to control tumors.

It is apparent that many modifications and variations of this invention as hereinabove set forth may be made without departing from the spirit and scope thereof. The specific embodiments described are given by way of example only and the invention is limited only by the terms of the appended claims.

A cell line, F36/22, as described herein has been deposited Mar. 1, 1983 with the American Type Culture Collection 12301 Parklawn Drive, Rockville, Md., and has been assigned accession number ATCC. No. HB8215. The invention described and claimed herein is not to be limited in scope by the cell line deposited, since the deposited embodiment is intended as a single illustration of one aspect of the invention and any equivalent cell lines which produce a functionally equivalent monoclonal antibody are within the scope of this invention. Indeed, various modifications of the invention in addition to those shown and described herein will become apparent to those skilled in the art from the foregoing description. Such modifications are also intended to fall within the scope of the appended claims.

TABLE XIII

COMPARISON OF PRE-TREATMENT TUMOR SIZE TO McAb F36/22 MEDIATED VOLUME REDUCTIONS[a]

| Antibody | Number of Mice/Group | Day 0 Range of Tumor Volume (mm) | Tumor Volumes[b] | | | | | | | |
| --- | --- | --- | --- | --- | --- | --- | --- | --- | --- | --- |
| | | | Day 0 | Day 1 | Day 2 | Day 3 | Day 4 | Day 5 | Day 6 | Day 7 |
| Group 1 (small tumors) | | | | | | | | | | |
| F36/22 | 6 | 26–42 | 34 ± 7 | 11 ± 8 | 9 ± 6 | 9 ± 5 | 5 ± 3 | 7 ± 3 | 6 ± 1 | 9 ± 4 |
| Control (γ3) | 5 | 25–49 | 38 ± 8 | 39 ± 2 | 46 ± 14 | 44 ± 16 | 51 ± 25 | 48 ± 30 | 45 ± 26 | 41 ± 20 |
| Level of significance (less than) | — | — | N.S.[d] | .001 | .001 | .001 | .001 | .001 | .001 | .001 |
| Group 2 (large tumors) | | | | | | | | | | |
| F36/22 | 6 | 60–80 | 74 ± 11 | 33 ± 16 | 27 ± 15 | 24 ± 20 | 25 ± 18 | 22 ± 16 | 22 ± 18 | 20 ± 17 |
| Control (γ3) | 3 | 80–88 | 84 ± 4 | 84 ± 6 | 85 ± 8 | 81 ± 7 | 74 ± 20 | 72 ± 15 | 69 ± 10 | 70 ± 14 |
| Level of significance (less than) | — | — | N.S.[d] | .001 | .001 | .001 | .001 | .001 | .001 | .001 |

[a]Mice with BT-20 tumors were pooled separately into groups of small and large tumors, the smaller tumors ranging from 26–49 mm$^3$, the larger tumors 60–88 mm$^3$. Each group was treated with 100 μg of McAB F36/22 for the experimental mice or 100 μg of control immunoglobulin for the control mice.
[b]All tumor volumes given as x ± SD, in mm$^3$.
[c]p values calculated by Student's t distribution.
[d]N.S., no statistically significant difference.

We claim:

1. An isolated carcinoma antigen isolated from breast or ovarian carcinoma comprising a mucin-like glycoprotein characterized by a molecular weight greater than about 669 Kd and least than 2,000 Kd as measured by gel filtration chromatography, an isoionic point of about pH 4.2 as determined by isoelectric focusing, a density of about 1.45 g/ml as determined by isopycnic ultracentrifugation in the absence of 4M guanidine hydrochloride, the presence of multiple antibody combining sites, a preferential reactivity with wheat germ lectin, as compared to reactivity with concanavalin A, peanut agglutinin and lentil lectin, said antigen having an epitope recognized by monoclonal antibody F36/22 assigned ATCC accession number HB 8215.

2. The ductal carcinoma of claim 1 which is purified.

3. The ductal carcinoma antigen of claim 2 which was purified using monoclonal antibody F36/22 having ATCC accession number HB 8215.

* * * * *

UNITED STATES PATENT AND TRADEMARK OFFICE
CERTIFICATE OF CORRECTION

PATENT NO. : 5,798,445

DATED : August 25, 1998

INVENTOR(S) : Tsann Ming Chu and Lawrence D. Papsidero

It is certified that error appears in the above-identified patent and that said Letters Patent is hereby corrected as shown below:

Column 5, line 53: "specifities" should read --specificities--.

Column 7, last paragraph (i.e., lines 58-67) is repetitive of the previous paragraph and should be deleted.

Column 8, line 25: "480 nm" should read --488 nm--.

Column 9, line 13: "1.45/ml" should read --1.45 g/ml--.

Column 45, line 30: "least than 2,000 KD" should read --less than 2,000KD--

Signed and Sealed this

Ninth Day of March, 1999

Attest:

Q. TODD DICKINSON

Attesting Officer

Acting Commissioner of Patents and Trademarks